(12) United States Patent
Morrell

(10) Patent No.: US 9,340,773 B2
(45) Date of Patent: May 17, 2016

(54) ANTIGEN-PRESENTING PLATELETS AND METHODS OF ELICITING AN IMMUNE RESPONSE

(75) Inventor: Craig Morrell, Rochester, NY (US)

(73) Assignee: University of Rochester, Rochester, NY (US)

( * ) Notice: Subject to any disclaimer, the term of this patent is extended or adjusted under 35 U.S.C. 154(b) by 159 days.

(21) Appl. No.: 14/000,959

(22) PCT Filed: Feb. 22, 2012

(86) PCT No.: PCT/US2012/026060
§ 371 (c)(1),
(2), (4) Date: Aug. 22, 2013

(87) PCT Pub. No.: WO2013/103362
PCT Pub. Date: Jul. 11, 2013

(65) Prior Publication Data
US 2013/0330311 A1    Dec. 12, 2013

Related U.S. Application Data

(60) Provisional application No. 61/445,241, filed on Feb. 22, 2011.

(51) Int. Cl.
| | |
|---|---|
| *A61K 35/12* | (2015.01) |
| *C12N 5/078* | (2010.01) |
| *A61K 35/15* | (2015.01) |
| *A61K 35/19* | (2015.01) |
| *G01N 33/50* | (2006.01) |
| *A61K 39/00* | (2006.01) |

(52) U.S. Cl.
CPC .............. *C12N 5/0644* (2013.01); *A61K 35/15* (2013.01); *A61K 35/19* (2013.01); *G01N 33/505* (2013.01); *A61K 2039/5154* (2013.01)

(58) Field of Classification Search
None
See application file for complete search history.

(56) References Cited

PUBLICATIONS

Youssefian et al., Blood. Jun. 1, 2002;99(11):4021-9.*
Higashihara et al., Blood. Feb. 1985;65(2):382-91.*
Mishima et al., Transfus Apher Sci. Feb. 2015;52(1):112-21. doi: 10.1016/j.transci.2014.11.001. Epub Nov. 11, 2014.*
Pavenski et al., Tissue Antigens. Apr. 2012;79(4):237-45. doi: 10.1111/j.1399-0039.2012.01852.x.*
Chapman et al., J Immunol. Jul. 15, 2012;189(2):916-23. doi: 10.4049/jimmunol.1200580. Epub Jun. 15, 2012.*
Belnoue et al., Control of pathogenic CD8+ T cell migration to the brain by IFN-a during experimental cerebral malaria, Parasite Immunology, vol. 30, No. 10, Oct. 2008, pp. 544-553.
Blann et al., The Platelet and Endothelium in HIV Infection, British Journal of Haematology, vol. 100, Issue 3, Mar. 1998, pp. 613-614.
Boshkov et al., HLA-DR expression by platelets in acute idiopathic thrombocytopenic purpura, British Journal of Haematology, vol. 81, No. 4, Aug. 1992, pp. 552-557.
Chaipan et al., DC-SIGN and CLEC-2 mediate human immunodeficiency virus type 1 capture by platelets, J. Virol., vol. 80, No. 18, Sep. 2006, 8951-8960.
Chapman et al., Platelets Present Antigen in the Context of MHC Class I, The Journal of Immunology, vol. 189, No. 2, Jun. 15, 2012, pp. 916-923.
Diacovo et al., Platelet-Mediated Lymphocyte Delivery to High Endothelial Venules, Science, vol. 273, No. 5272, Jul. 12, 1996, pp. 252-255.
Elton et al., Physical and functional interaction between cell-surface calreticulin and the collagen receptors integrin alpha2beta1 and glycoprotein VI in human platelets, Thromb. Haemost., vol. 88, No. 4, pp. 648-654.
Elzey, The emerging role of platelets in adaptive immunity, Cell Immunology, vol. 238, No. 1, Nov. 2005, pp. 1-9.
Fajardo, Malarial Parasites in Mammalian Platelets, Nature, vol. 243, Jun. 1, 1973, pp. 298-299.
Gawaz et al., Platelets in inflammation and atherogenesis, Journal of Clinical Investigation, vol. 115, No. 12, Dec. 1, 2005, pp. 3378-3384.
Gawaz, Role of platelets in coronary thrombosis and reperfusion of ischemic myocardium, Cardiovascular Research, vol. 61, 2004, pp. 498-511.
Grau et al., Platelet Accumulation in Brain Microvessels in Fatal Pediatric Cerebral Malaria, Journal of Infectious Diseases, vol. 187, No. 3, Feb. 1, 2003, pp. 461-466.
Hafalla et al., Protective and pathogenic roles of CD8+ T cells during malaria infection, Parasite Immunology, vol. 28, No. 1-2, 2006, pp. 15-24.
Han et al., The Ultrastructure of Megakaryocytes and Blood Platelets in the Rat Spleen, Anatomical Record, vol. 149, Jun. 1964, pp. 251-267.
Hunt et al., Immunopathogenesis of Cerebral Malaria, International Journal of Parasitology, vol. 36, No. 5, May 2006, pp. 569-582.
Iannacone et al., Platelets Mediate Cytotoxic T Lymphocyte-induced Liver Damage, Nature Medicine, vol. 11, No. 11, Nov. 2005, pp. 1167-1169.
Idro et al., Burden, features, and outcome of neurological involvement in acute falciparum malaria in Kenyan children, JAMA, vol. 297, No. 20, May 23, 2007, pp. 2232-2240.
Karl et al., A comparative study of a flow-cytometry-based assessment of in vitro Plasmodium falciparum drug sensitivity, Malaria Journal, vol. 8, Dec. 14, 2009, 294 pages.
Khandoga et al., CD4+ T cells contribute to postischemic liver injury in mice by interacting with sinusoidal endothelium and platelets, Hepatology, vol. 43, No. 2, Feb. 2006, pp. 306-315.

(Continued)

*Primary Examiner* — Michael Szperka
(74) *Attorney, Agent, or Firm* — Kilpatrick Townsend & Stockton, LLP

(57) ABSTRACT

Provided herein are methods of producing an antigen-presenting platelet. Also provided herein are methods of eliciting an immune response in a subject using the antigen-presenting platelets described herein. Also provided are methods of screening for an immune response elicited by an antigen-presenting platelet. Further provided are isolated populations of platelets that present a selected antigen produced by the methods described herein.

8 Claims, 19 Drawing Sheets

(56) References Cited

PUBLICATIONS

Kirk, Platelets Influence Vascularized Organ Transplants from Start to Finish, American Journal of Transplantation, vol. 9, No. 1, Jan. 2009, pp. 14-22.

Kraemer et al., PI3 kinase-dependent stimulation of platelet migration by stromal cell-derived factor 1 (SDF-1), J. Mol. Med. (Berl)., vol. 88, issue 12, Dec. 2010, pp. 1277-1288.

Langer et al., Adherent Platelets Recruit and Induce Differentiation of Murine Embryonic Endothelial Progenitor Cells to Mature Endothelial Cells In Vitro, Circulation Research, vol. 98, 2006, pp. e2-e10.

Lee et al., Effect of platelet-associated virus on assays of HIV-1 in plasma, Science, vol. 262, 1993, pp. 1585-1586.

Lou et al., Platelets Play an Important Role in TNF-Induced Microvascular Endothelial Cell Pathology, American Journal of Pathology, vol. 151, No. 5, Nov. 1997, 9 pages.

Lundie et al., Blood-stage Plasmodium infection induces CD8 T lymphocytes to parasite-expressed antigens, largely regulated by CD 8 dendritic cells, PNAS, vol. 105, No. 38, Sep. 23, 2008, pp. 14509-14514.

Male et al., Phagocytosis of liposomes by human platelets, PNAS, vol. 89, Oct. 1992, pp. 9191-9195.

Mannel et al., Role of platelet adhesion in homeostasis and immunopathology, J. Clin. Pathol: Mol. Pathol., vol. 50, 1997, pp. 175-185.

Massberg et al., Platelets secrete stromal cell-derived factor $1\alpha$ and recruit bone marrow-derived progenitor cells to arterial thrombi in vivo, J. Exp Med., vol. 203, No. 5, Apr. 17, 2006, pp. 1221-1233.

Matsushita et al., Nitric Oxide Regulates Exocytosis by S-Nitrosylation of N-ethylmaleimide-Sensitive Factor, Cell, vol. 115, No. 2, Oct. 17, 2003, pp. 139-150.

Mitchell et al., Circulating microRNAs as stable blood-based markers for cancer detection, PNAs, vol. 105, No. 30, Jul. 29, 2008, pp. 10513-10518.

Miyakoda et al., Malaria-specific and nonspecific activation of CD8+ T cells during blood stage of Plasmodium berghei infection, J. Immunol., vol. 181, issue 2, Jul. 15, 2008, pp. 1420-1428.

Morrell et al., Glutamate mediates platelet activation through the AMPA receptor, J. Exp. Med., vol. 205 No. 3, Feb. 18, 2008, pp. 575-584.

Morrell et al., Low levels of linkage disequilibrium in wild barley (*Hordeum vulgare* ssp. spontaneum) despite high rates of self-fertilization, PNAS, vol. 102, No. 7, Feb. 15, 2005, pp. 2442-2447.

Ostrowska et al., Lactacystin, a Specific Inhibitor of the Proteasome, Inhibits Human Platelet Lysosomal Cathepsin A-like Enzyme, Biochem. Biophys. Res. Commun., vol. 234, issue 3, May 29, 1997, pp. 729-732.

Ostrowska et al., Human platelet 20S proteasome: inhibition of its chymotrypsin-like activity and identification of the proteasome activator PA28. A preliminary report, Platelets, vol. 14 No. 3, 2003, pp. 151-157.

International Application No. PCT/US2012/026060, International Preliminary Report on Patentability mailed on Sep. 6, 2013, 6 pages.

International Application No. PCT/US2012/026060, International Search Report and Written Opinion mailed on Oct. 23, 2012, 9 pages.

Perkash et al., Enhanced parasitization of platelets by plasmodium berghei yoelii, Trans. R. Soc. Trop. Med. Hyg., vol. 78, No. 4, 1984, pp. 451-455.

Renia et al., Pathogenic T cells in cerebral malaria, International Journal for Parasitology, vol. 36, issue 5, May 2006, pp. 547-554.

Rowley et al., Genome-wide RNA-seq analysis of human and mouse platelet transcriptomes, Blood, vol. 118, No. 14, Oct. 6, 2011, pp. e101-e111.

Schulz et al., Identification of novel downstream targets of platelet glycoprotein VI activation by differential proteome analysis: implications for thrombus formation, Blood, vol. 115, Jan. 27, 2010, 38 pages.

Semple et al., Differences in serum cytokine levels in acute and chronic autoimmune thrombocytopenic purpura: relationship to platelet phenotype and antiplatelet T-cell reactivity, Blood, vol. 87, issue10, May 1, 1996, pp. 4245-4254.

Semple et al., Platelets and the immune continuum, Nature Reviews Immunology, vol. 11, Apr. 2011, pp. 264-274.

Srivastava et al., Platelet Factor 4 Mediates Inflammation in Experimental Cerebral Malaria, Cell Host & Microbe, vol. 4, Aug. 14, 2008, pp. 179-187.

Srivastava et al., Platelet Factor 4 Regulation of Monocyte KLF4 in Experimental Cerebral Malaria, PLoS One, vol. 5 issues, May 2010, 11 pages.

Swaim et al., Platelets Contribute to Allograft Rejection through Glutamate Receptor Signaling, The Journal of Immunology, vol. 185, Oct. 20, 2010, 9 pages.

Van Der Heyde et al., A unified hypothesis for the genesis of cerebral malaria: sequestration, inflammation and hemostasis leading to microcirculatory dysfunction, Trends Parasitol., vol. 22, issue 11, Nov. 2006, pp. 503-508.

Van Der Heyde et al., Platelet depletion by anti-CD41 (IIb) mAb injection early but not late in the course of disease protects against Plasmodium berghei pathogenesis by altering the levels of pathogenic cytokines, Blood, vol. 105, No. 5, Mar. 1, 2005, pp. 1956-1963.

Wassmer et al., Platelets Potentiate Brain Endothelial Alterations Induced by Plasmodium falciparum, Infection and Immunity, vol. 74, No. 1, Jan. 2006, pp. 645-653.

Wiwanitkit, Platelet CD61 Might Have an Important Role in Causing Hemorrhagic Complication in Dengue Infection, Clin. Appl. Thromb. Hemost., vol. 11, No. 1, 2005, p. 112.

Xu et al., Platelet-derived or soluble CD154 induces vascularized allograft rejection independent of cell-bound CD154, J. Clin. Invest., vol. 116, issue 3, Mar. 1, 2006, pp. 769-774.

Youssefian et al., Host defense role of platelets: engulfment of HIV and *Staphylococcus aureus* occurs in a specific subcellular compartment and is enhanced by platelet activation, Blood, vol. 99, No. 11, Jun. 1, 2002, pp. 4021-4029.

\* cited by examiner

SEQUENCE LISTING

```
<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Ser Ile Ile Asn Phe Glu Lys Leu
1               5

<210> SEQ ID NO 2
<211> LENGTH: 237
<212> TYPE: PRT
<213> ORGANISM: Artificial Sequence
<220> FEATURE:
<223> OTHER INFORMATION: Synthetic Construct

<400> SEQUENCE: 2

Val Glu Ser Gln Thr Asn Gly Ile Ile Arg Asn Val Leu Gln Pro Ser
1               5                   10                  15

Ser Val Asp Ser Gln Thr Ala Met Val Leu Val Asn Ala Ile Val Phe
                20                  25                  30

Lys Gly Leu Trp Glu Lys Thr Phe Lys Asp Glu Asp Thr Gln Ala Met
            35                  40                  45

Pro Phe Arg Val Thr Glu Gln Glu Ser Lys Pro Val Gln Met Met Tyr
        50                  55                  60

Gln Ile Gly Leu Phe Arg Val Ala Ser Met Ala Ser Glu Lys Met Lys
65                  70                  75                  80

Ile Leu Glu Leu Pro Phe Ala Ser Gly Thr Met Ser Met Leu Val Leu
                85                  90                  95

Leu Pro Asp Glu Val Ser Gly Leu Glu Gln Leu Glu Ser Ile Ile Asn
                100                 105                 110

Phe Glu Lys Leu Thr Glu Trp Thr Ser Ser Asn Val Met Glu Glu Arg
            115                 120                 125

Lys Ile Lys Val Tyr Leu Pro Arg Met Lys Met Glu Glu Lys Tyr Asn
        130                 135                 140

Leu Thr Ser Val Leu Met Ala Met Gly Ile Thr Asp Val Phe Ser Ser
145                 150                 155                 160

Ser Ala Asn Leu Ser Gly Ile Ser Ser Ala Glu Ser Leu Lys Ile Ser
                165                 170                 175
```

-continued

```
Gln Ala Val His Ala Ala His Ala Glu Ile Asn Glu Ala Gly Arg Glu
            180                 185                 190
Val Val Gly Ser Ala Glu Ala Gly Val Asp Ala Ala Ser Val Ser Glu
            195                 200                 205
Glu Phe Arg Ala Asp His Pro Phe Leu Phe Cys Ile Lys His Ile Ala
            210                 215                 220
Thr Asn Ala Val Leu Phe Phe Gly Arg Cys Val Ser Pro
225                 230                 235

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Met Ser Val Leu Gly
1               5
```

ANTIGEN-PRESENTING PLATELETS AND METHODS OF ELICITING AN IMMUNE RESPONSE

CROSS REFERENCE TO RELATED APPLICATIONS

This application claims the benefit of U.S. Provisional Application No. 61/445,241, filed on Feb. 22, 2011, which is incorporated herein by reference in its entirety.

STATEMENT REGARDING FEDERALLY FUNDED RESEARCH

This invention was made with government funding under Grant Nos. RO1HL093179, RO1HL093179-02S109, and RO1HL094547 from the National Institutes of Health. The government has certain rights in this invention.

BACKGROUND

Platelets are small (~1 µM), anucleate, megakaryocte-derived circulating cells that are numerous in the blood (~200,000 µL in humans). Platelets have a role as the cellular mediators of hemostasis.

SUMMARY

Provided are methods of producing an antigen-presenting platelet. The methods comprise isolating a platelet from a subject and incubating the platelet with an antigen. Incubation of the platelet with the antigen results in the production of the antigen-presenting platelet.

Also provided are methods of eliciting an immune response in a subject. The method comprises providing antigen-presenting platelets, wherein the platelets present a selected antigen and administering to the subject the antigen-presenting platelets. Administration of the antigen-presenting platelets elicits an immune response in the subject.

Also provided are methods of screening for an immune response elicited by an antigen-presenting platelet. The methods comprise administering to a subject an antigen-presenting platelet and determining a level of expression of interleukin-2 (IL2). An increase in a level of expression of IL2 as compared to a control indicates an immune response.

Also provided are in vitro methods of screening for an immune response elicited by an antigen-presenting platelet. The methods comprise contacting a T-cell with an antigen-presenting platelet and determining a level of expression of IL2. An increase in a level of expression of IL2 as compared to a control indicates an immune response.

Further provided are isolated population of platelets that present a selected antigen. The antigen can, for example, be selected from the group consisting of a viral antigen, a bacterial antigen, a cancer antigen, and a parasitic antigen.

The details of one or more embodiments are set forth in the accompanying drawings and the description below. Other features, objects, and advantages will be apparent from the description and drawings, and from the claims.

DESCRIPTION OF DRAWINGS

FIG. 1 shows that platelets express molecules necessary for antigen presentation.

FIG. 2 shows that platelets promote T-cell co-stimulation and present antigen.

FIG. 3 shows that platelets present antigen to T-cells.

FIG. 4 shows that platelets promote T-cell co-stimulation in *P. berghei* infection.

FIG. 5 shows platelets increase MHCI expression in ECM.

FIG. 6 shows that platelets can be used to stimulate naïve T cells in vivo in a mouse skin graft model.

DETAILED DESCRIPTION

Figure 1A:
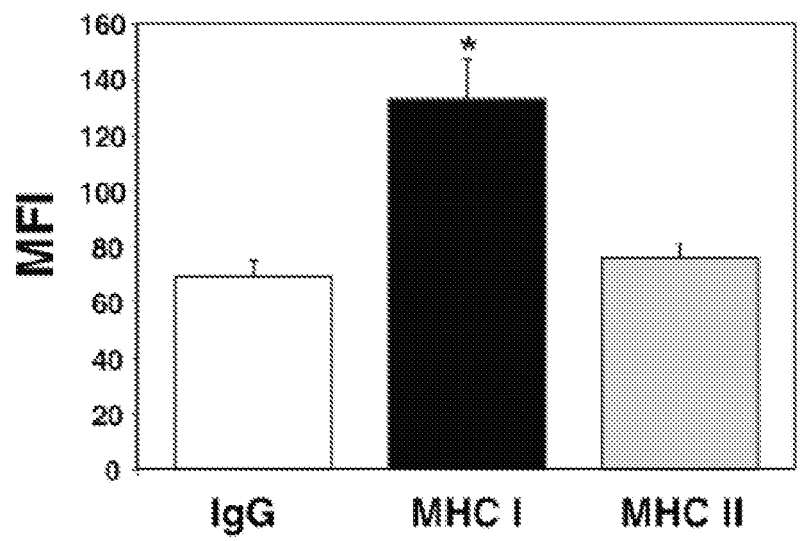
FIG. 1A is a graph demonstrating quantification of the presentation of MHC class 1 molecules (n=4±SD, *P=1×10$^{-8}$).

Provided are methods of producing an antigen-presenting platelet. The methods comprise isolating a platelet from a subject and incubating the platelet with an antigen. Incubation of the platelet with the antigen results in the production of the antigen-presenting platelet.

Optionally, the method further comprises incubating the platelets with an activator. The activator can, for example, be selected from the group consisting of thrombin, ADP, and collagen. Optionally, the activator can be selected from the group consisting of agonists of thrombin receptors, agonists of purigenic receptors, agonists of thrombaxane receptors, agonists of collagen receptors, agonists of glycoprotein (GP) Ib receptors, and agonists of active GPIIb/IIIa receptors.

Optionally the antigen is incubated with the platelets for at least 15 minutes. The antigen can, for example, be incubated with the platelets for at least 20, 25, 30, 45, 60, 90, 120, 180, 240, 300, or 360 minutes. Those of skill in the art readily understand how to determine the amount of incubation time for an antigen with the platelets.

Also provided are methods of eliciting an immune response in a subject. The methods comprise providing antigen-presenting platelets, wherein the platelets present a selected antigen and administering to the subject the antigen-presenting platelets. Administration of the antigen presenting platelets elicits an immune response in the subject.

Optionally, the method further comprises administering an adjuvant to the subject. Adjuvants include metallic salts, such as aluminum salts, and are well known in the art as providing a safe excipient with adjuvant activity. The mechanism of action of these adjuvants is believed to include the formation of an antigen deposit such that the antigen may stay at the site of injection after administration and also the formation of antigen/metallic salt complexes which are more easily taken up by antigen presenting cells. In addition to aluminum, other metallic salts have been used to adsorb antigens, including salts of zinc, calcium, cerium, chromium, iron, and beryllium. The hydroxide and phosphate salts of aluminum are the most common.

Optionally, the method further comprises administering to the subject an antigen-presenting cell. The antigen-presenting cell can, for example, be a dendritic cell.

The antigen-presenting platelets can, for example, be produced from platelets isolated from the same or a different subject. Thus, the platelets can be derived from the subject that is administered the antigen-presenting platelets, of the platelets can be derived from a donor that differs from the recipient.

Platelets can be isolated from the blood of the subject. Methods for isolating platelets are known in the art, see, e.g., Ganguly and Sonnichsen, J. Clin. Pathol. 26(8):635-7 (1973); Hoffman et al., Am. J. Clin. Pathol. 98(5):531-3 (1992); and Watson et al., Platelets: A Practical Approach, Oxford University Press (1996).

Optionally, the antigen-presenting platelets are administered to the subject at least two times, for example, to boost the immune response of the subject to the selected antigen. The second administration of the antigen-presenting platelets can, for example, be at least five, six, seven, eight, nine, ten, eleven, twelve, thirteen, or fourteen days after the first administration. One of skill in the art can determine the optimum prime and boost regimen.

Optionally, the antigen is selected from the group consisting of a viral antigen, a bacterial antigen, a cancer antigen, a fungal antigen, a prion antigen, and a parasitic antigen. Antigens are well known in the art. Optionally, the antigen is a polypeptide or glycoprotein, but an antigen is any molecule that is recognized by the immune system. A viral antigen can, for example, include any viral antigenic molecule or inactivated or attenuated virus (e.g., an envelope protein, a structural protein, and/or a capsid protein). The viral antigen can, for example, be selected from the group consisting of Dengue virus envelope protein antigens, NS1 antigen, Hepatits C virus core protein antigen, Toxoplasma p24 antigen, Toxoplasma p29 antigen, Toxoplasma p30 antigen, Measles virus antigens, Borelia p41 antigen, and HIV gp120 antigen. A bacterial antigen can, for example, include any bacterial antigenic molecule or inactivated or attenuated bacterium. The bacterial antigen can, for example, be a *Plasmodium* pfEMP1 antigen or HSP70 polypeptide antigens. A fungal antigen can, for example, include any fungal antigenic molecule or inactivated or attenuated fungus. A prion antigen can comprise any prion antigenic molecule or inactivated or attenuated prion. A parasitic antigen can, for example, include any parasitic antigen molecule or inactivated or attenuated parasite. The parasitic antigen can, for example, be a malarial antigen. As a general rule, surface antigens are most useful for provoking an immune response and can include cellular lipids, proteins, proteoglycans or portions thereof.

A cancer antigen can, for example, include an antigenic portion of a polypeptide that is overexpressed in the cancer, an antigenic portion of a polypeptide that is expressed on the cell surface of the cancer cells, or an antigenic portion of the proteoglycans or lipids on the cell surface of the cells of the cancer. The cancer antigen can, for example, be selected from the group consisting of prostate specific antigen, melanoma associated antigen, tyrosinase antigen, MUC-1 antigen, CA-125 antigen, CEA antigen, and AFP antigen. Cancer antigens are known in the art, see, e.g., Sonpavde et al., Urol. Oncol. 25:451-9 (2007); Suri, Expert Opin. Biol. Ther. 6:379-89 (2006); Saleh et al., Curr. Pharm. Des. 11:3461-73 (2005); Bensalah et al., Prostate Cancer Prostatic Dis. 11:112-20 (2008); Disis et al., Breast Dis. 20:3-11 (2004); McNeel, Cancer Chemother. Biol. Response Modif. 22:247-61 (2005); Jager et al., Curr. Opin. Immunol. 14; 178-82 (2002); Obata et al., Breast Cancer 6:305-11 (1999), which are incorporated herein for cancer antigens and methods of making and using them.

One of skill in the art will readily understand how to select the proper antigen for eliciting an immune response, see, e.g., Zepp, Vaccine 28(Suppl 3):C14-24 (2010); Walters and Mobley, Expert Rev. Proteomics 7(2):181-4 (2010); Goodman and Draper, Ann. Trop. Med. Parasitol. 104(3):189-211 (2010); Weiner et al., Cancer Prev. Res. 3(4):410-5 (2010); Shumway et al., Biodrugs 23(5):277-87 (2009); Rammensee et al., Immunol. Rev. 188:164-76 (2002).

Also provided are methods of screening for an immune response elicited by an antigen-presenting platelet. The methods comprise administering to a subject an antigen-presenting platelet and detecting an immune response or by determining a level of expression of interleukin-2 (IL2). An increase in a level of antibody production to the selected antigen or an increase in the expression of IL2 as compared to a control indicates an immune response. As used herein, control refers to an untreated sample from the same or different subject or a sample from the same subject before administration of the antigen-presenting platelets. A control can include a known value or can be a sample run in parallel with the experimental sample.

Also provided are in vitro methods of screening for an immune response elicited by an antigen-presenting platelet. The methods comprise contacting a T-cell with an antigen-presenting platelet and determining a level of expression of IL2. An increase in the level of expression of IL2 as compared to a control indicates an immune response.

Optionally, the level of expression of IL2 is determined by detecting IL2 RNA. The level of IL2 RNA is detected using an assay selected from the group consisting of a microarray analysis, a gene chip, a Northern blot, an in situ hybridization assay, a RT-PCR assay, a one-step PCR assay, and a quantitative real-time (qRT)-PCR assay. Optionally, the level of expression of IL2 is determined by detecting IL2 protein. The level of IL2 protein is detected using an assay selected from the group consisting of a Western blot assay, an ELISA assay, an EIA assay, a RIA assay, and a protein array assay. The analytical techniques to determine RNA or protein are known. See, e.g. Sambrook et al., Molecular Cloning: A Laboratory Manual, $3^{rd}$ Ed., Cold Spring Harbor Press, Cold Spring Harbor, N.Y. (2001).

Further provided is an isolated population of platelets that present a selected antigen. Optionally, the antigen is selected from the group consisting of a viral antigen, a bacterial antigen, a cancer antigen, a fungal antigen, a prion antigen, and a parasitic antigen. The antigen is selected and used for incubation with the platelets to produce a population of platelets that present the selected antigen. Not every platelet in the population need to present the antigen. Optionally, at least about 50, 60, 70, 80, 90, 100%, or any amount in between present the selected antigen. The isolated population of platelets can, for example, be made by any of the methods described herein.

Provided herein are compositions containing the population of selective antigen presenting platelets and a carrier (e.g., a pharmaceutically acceptable carrier) described herein. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject. Optionally, the composition can further comprise an adjuvant. Optionally, the composition can further comprise antigen presenting cells (e.g., dendritic cells). Optionally, the composition can further comprise the selected antigen.

Suitable carriers and their formulations are described in *Remington: The Science and Practice of Pharmacy*, $21^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the compositions disclosed herein, to humans or other subjects.

The compositions are administered in a number of ways depending on whether local or systemic treatment is desired, and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. Optionally, the composition is administered by oral inhalation, nasal inhalation, or intranasal mucosal administration. Administration of the compositions by inhalant can be through the nose or mouth via delivery by spraying or droplet mechanism, for example, in the form of an aerosol. A form of administration that results in an immune response can be used by one of skill in the art to optimize the response.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, antioxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As used throughout, subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with or at risk of developing an infection, a disease, or disorder (e.g., a viral infection, a bacterial infection, a fungal infection, a prion infection, or cancer). The term patient or subject includes human and veterinary subjects.

For purposes of vaccines, the subject may be healthy and without higher risk than the general public. A subject at risk of developing an infection, however, can be predisposed to contracting an infection (e.g., by having unprotected sex, sharing unsterilized needles, or being in an environment that facilitates the passage of an infection). A subject at risk of developing a disease or disorder can be genetically predisposed to the disease or disorder, e.g., have a family history or have a mutation in a gene that causes the disease or disorder, or show early signs or symptoms of the disease or disorder. A subject currently with an infection, disease, or disorder has one or more than one symptom of the infection, disease, or disorder and may have been diagnosed with the disease or disorder.

The methods and agents as described herein are useful for both prophylactic and therapeutic treatment. For prophylactic use, a therapeutically effective amount of the agents described herein are administered to a subject prior to onset (e.g., before obvious signs of infection, disease, or disorder) or during early onset (e.g., upon initial signs and symptoms of infection, disease, or disorder). Prophylactic administration can occur for several days to years prior to the manifestation of symptoms of the infection, disease or disorder. Prophylactic administration can be used, for example, in the preventative treatment of subjects diagnosed with a genetic predisposition to cancer. Therapeutic treatment involves administering to a subject a therapeutically effective amount of the agents described herein after diagnosis or development of infection, disease, disorder.

According to the methods taught herein, the subject is administered an effective amount of the agent, e.g., the antigen-presenting platelets. The terms effective amount and effective dosage are used interchangeably. The term effective amount is defined as any amount necessary to produce a desired physiologic response (i.e., an immune response). Effective amounts and schedules for administering the agent may be determined empirically, and making such determinations is within the skill in the art. The dosage ranges for administration are those large enough to produce the desired effect (e.g., eliciting an immune response to the antigen of interest). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of the infection or disease or a symptom of the infection or disease by eliciting an immune response in the subject. Thus in the disclosed method, treatment can refer to a 10%, 20%, 30%, 40%, 50%, 60%, 70%, 80%, 90%, or 100% reduction in the severity of an established infection or disease or a symptom of the infection or disease. For example, a method for treating an infection or disease is considered to be a treatment if there is a 10% reduction in one or more symptoms of the infection or the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the infection or disease or symptoms of the infection or disease.

As used herein, the terms prevent, preventing, and prevention of an infection, disease, or disorder refers to an action, for example, administration of a therapeutic agent (e.g., a composition disclosed herein), that occurs before or at about the same time a subject begins to show one or more symptoms of the infection, disease, or disorder, which inhibits or delays onset or exacerbation of one or more symptoms of the infection, disease, or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination of the infection, disease, or disorder.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Materials and Methods

Reagents:

Antibodies against MHC, CD40, CD86, CD80, ICOSL, MHCI-OVA complex, CD3, CD28 and CD69 were purchased from eBiosciences (San Diego, Calif.). All ELISAs were purchased from R&D Systems (Minneapolis, Minn.). SIINFEKL (SEQ ID NO:1) peptide was purchased from Bachem (Torrance, Calif.). Platelet depleting and control IgG antibodies were purchased from Emfret Analytics (Wurzberg, Germany). Ovalbumin, $PGE_2$ and thrombin were purchased from Sigma (St. Louis, Mo.) and U46619 from Tocris (Ellisville, Mo.). DQ-Ovalbumin was purchased from Invitrogen (Carlsbad, Calif.).

Methods:

All mice used were on a C57B16/J background and purchased from Jackson Labs (Bar Harbor, Me.). Platelets from mice and humans were isolated as previously described (Matsushita et al., Cell 115:139 (2003); Morrell et al., Proc. Natl. Acad. Sci. USA 102:3782 (2005); Morrell et al., J. Exp. Med. 205:575 (2008)) using University of Rochester School of Medicine approved animal and human protocols. For all experiments using mouse platelets, platelets were prepared as washed platelets with $PGE_2$ used to prevent activation in the wash step and resuspended in calcium and magnesium free Tyrodes solution. Human platelet rich plasma (PRP) was isolated and resuspended in Tyrodes solution at a 1:20 ratio as previously described (Morrell et al., Proc. Natl. Acad. Sci. USA 102:3782 (2005); Morrell et al., J. Exp. Med. 205:575 (2008)). Platelets were incubated with antibodies for 20-30 minutes at room temperature and fixed with 2% formalin before flow cytometry using a BDFacs Canto instrument (BDBiosciences; Franklin Lakes, N.J.) and analysis using FloJo software (FlowJo; Ashland, Oreg.).

Mouse T-cells from spleens and lymph nodes were isolated using a negative selection T-cell enrichment kit from Stem-Cell Technology (Vancouver, BC, Canada). Plates were coated with anti-CD3 antibody prior to plating T-cells and incubating in RPMI with 5% FBS and penicillin/streptomycin. T-cells were incubated with washed platelets in an approximately physiologic ratio of 1:20.

In vivo platelet clearance assay used mouse platelets incubated with 10 µM of CFDA for 20 minutes. Platelets were washed and then injected intravenous via the retro-orbital plexus into recipient mice.

In P. berghei infections mice were injected intraperitoneal with approximately 500,000 infected mouse RBCs. Mice were platelet depleted by an intraperitoneal injection with 50 µg of platelet depleting antibody or control IgG. This antibody has been shown to greatly depress platelet counts for approximately 4 days (Swaim et al., J. Immunol. 185:6999 (2010)). All mouse plasma was collected by bleeding into EDTA coated tubes and spinning at 5000 rpm for 10 minutes.

In platelet vaccine studies OVA peptide or control PBS was added to washed platelets. The platelets were stimulated with thrombin and incubated for 2 hours. Platelets were then washed in the presence of $PGE_2$ and resuspended in Tyrodes buffer before $1 \times 10^7$ platelets in a volume of 100 µL were injected into WT mice via the retro-orbital plexus. Parasitemia was measured by isolating RBC and incubating with Sybr Green to label iRBC and the number determined by flow cytometry using described methods (Karl et al., Malar. J. 8:294 (2009)) and confirmed by Giemsa stained blood smears.

All statistics are shown as standard deviation and P value determined by a standard Student's T-Test.

Results

Figure 1B:
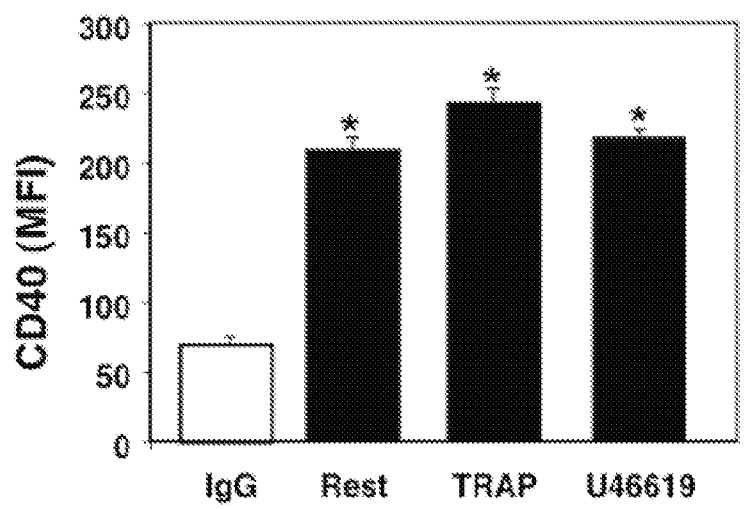
FIG. 1B is a graph demonstrating quantification of CD40 in resting or activated human platelets. Resting or activated human platelets (2 µM TRAP or U46619) were incubated with control IgG or anti-CD40 antibody (n=4±SD, *P=8×10$^{-7}$ vs. IgG).
Figure 1C:
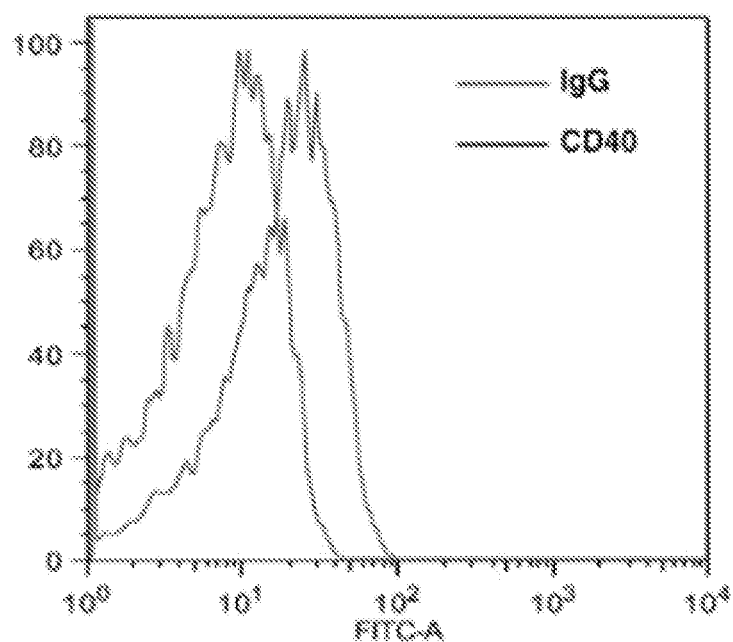
FIG. 1C is a graph demonstrating that platelets express co-stimulatory molecules. Human platelets were incubated with control IgG or anti-CD40 antibody. Platelets express CD40 (representative).
Figure 1D:
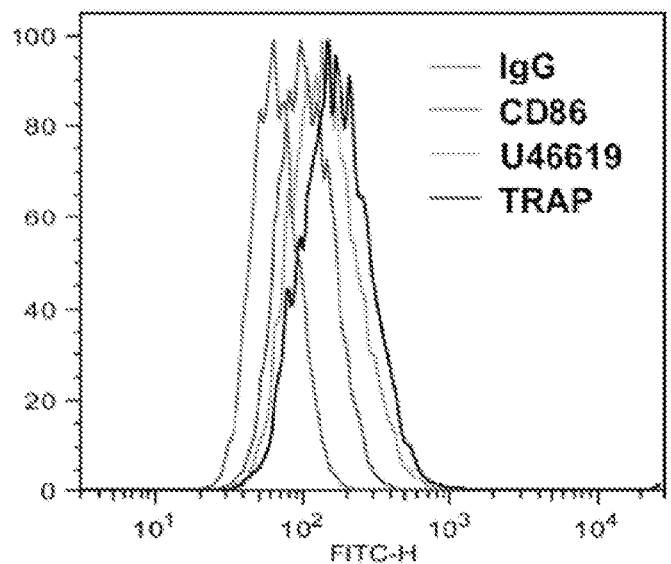
FIG. 1D is a graph demonstrating that human platelets express CD86, which is increased upon stimulation of the platelets.
Figure 1E:
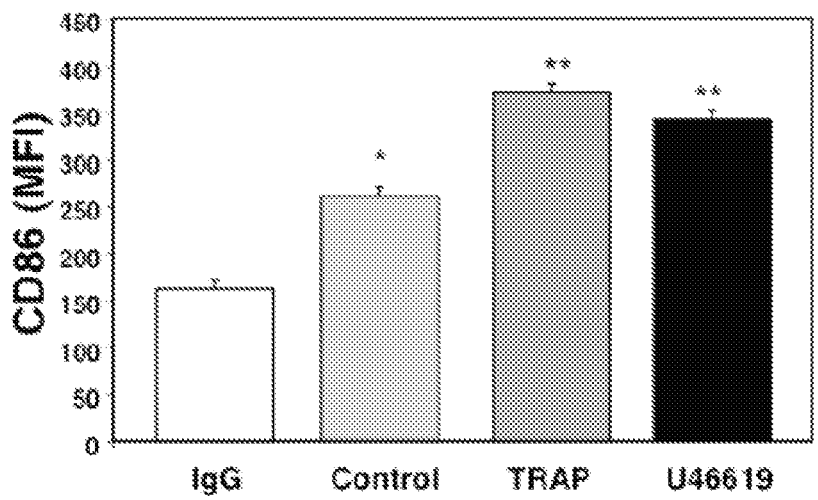
FIG. 1E is a graph demonstrating quantification of the expression of CD86 (n=4±SD, *P<0.005 vs IgG).
Figure 1F:
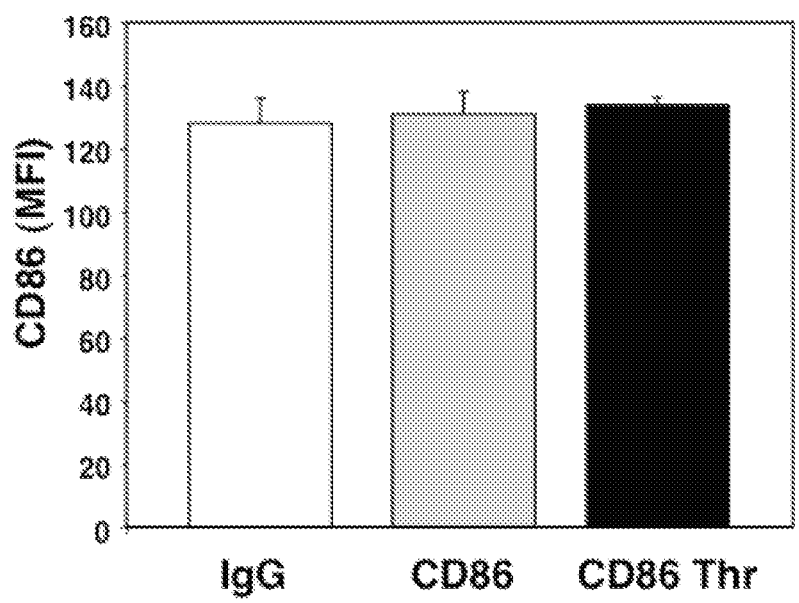
FIG. 1F is a graph demonstrating that mouse platelets do not express CD86 (n=4±SD).
Figure 1G:
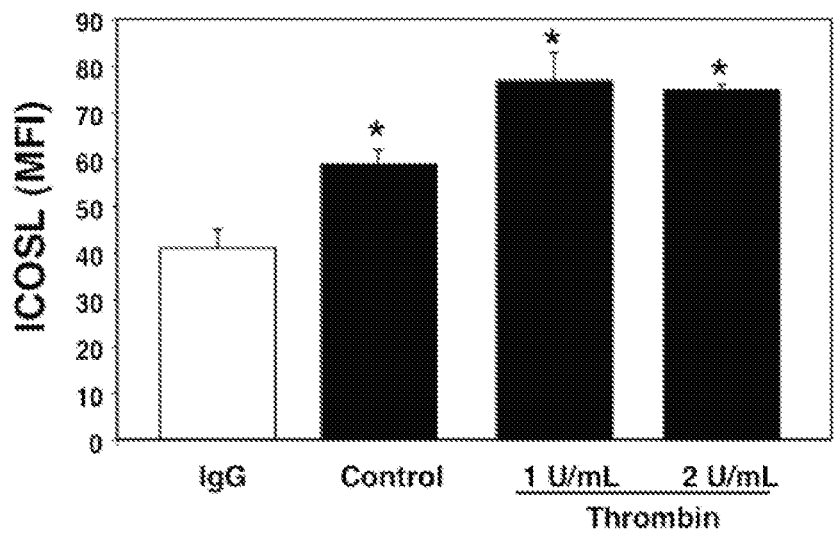
FIG. 1G is a graph demonstrating quantification of the expression of inducible T-cell co-stimulator ligand (ICOSL). Platelets were incubated with control PBS or activated with thrombin (n=4±SD, *P=0.003).

Platelets possess the molecular machinery necessary to be an antigen presenting cell (APC). Platelets express MHC class I, but under normal conditions do not express class II (FIG. 1A). Platelets also express T-cell co-stimulatory molecules. It was found that CD40 increases slightly with activation (FIGS. 1B and 1C). It was also found that human platelets express the strong co-stimulatory molecule CD86 (B7.2) on their surface, and CD86 surface expression is increased with platelet activation (FIGS. 1D and 1E). (Platelet activation and stimulation are used interchangeably to mean taking platelets from a resting state to an activated state, which is associated with degranulation and adhesion molecule up regulation). However, mouse platelets do not express CD86 (FIG. 1F), and neither mouse nor human platelets express CD80. Other costimulatory molecules such as inducible T-cell co-stimulator ligand (ICOSL) are expressed by platelets (FIG. 1G).

Figure 2A:
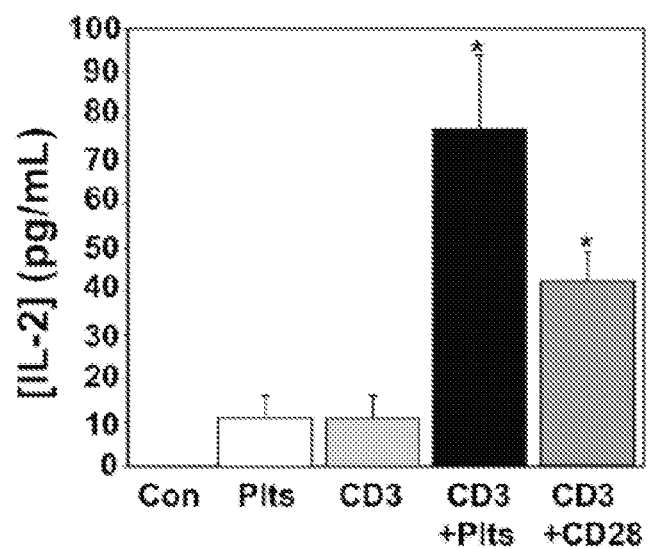
FIG. 2A is a graph demonstrating quantification of IL-2 in T-cells. T-cells were incubated in anti-CD3 antibody (2 µg/ml). IL-2 expression was measured by ELISA (n=4±SD, +P=0.004 vs. Control).
Figure 2B:
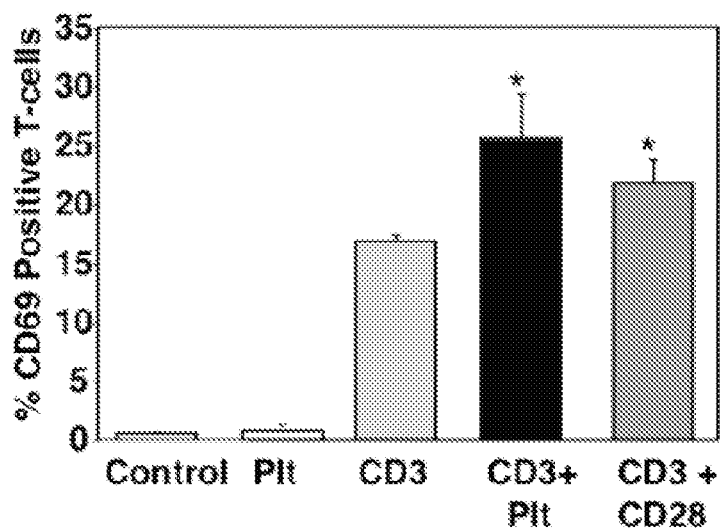
FIG. 2B is a graph demonstrating quantification of the percentage of CD69 positive T-cells. CD69 expression was measured by FACS (n=4±SD, *P=0.004 vs. Control).

It was next determined whether platelets provide T-cell co-stimulation (signal 2). Mouse T-cells were incubated overnight with control buffer, platelets only, with anti-CD3 antibody only (signal 1), or with anti-CD3 antibody and platelets, or anti-CD28 antibody (signal 2). T-cells incubated with anti-CD3 and CD28 antibodies (positive control) and anti-CD3 and platelets had significantly increased IL-2 production and CD69 expression compared to CD3 alone (FIGS. 2A and 2B). This demonstrates that platelets promote T-cell co-stimulation.

Figure 2C:
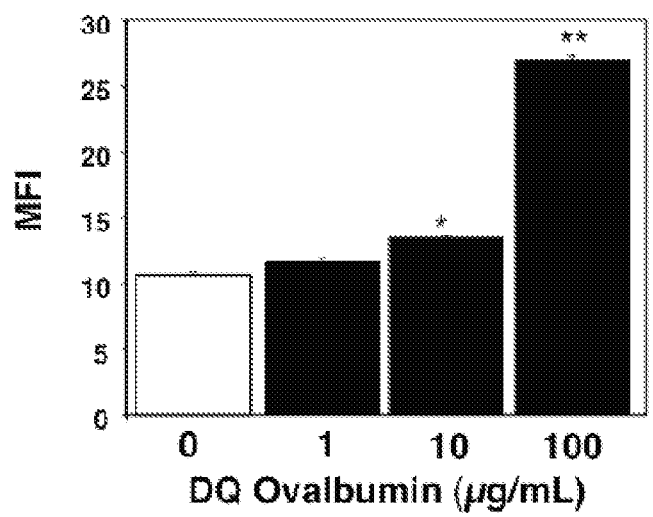
FIG. 2C is a graph demonstrating quantification of fluorescence in platelets incubated with DQ-Ovalbumin. Platelets were incubated with DQ-Ovalbumin which has increased fluorescence when degraded. Fluorescence was determined by fluorescence activated cell sorting (FACS) (n=4±SD, *P<0.00038, *P<1.27× 10$^{-6}$).
Figure 2D:
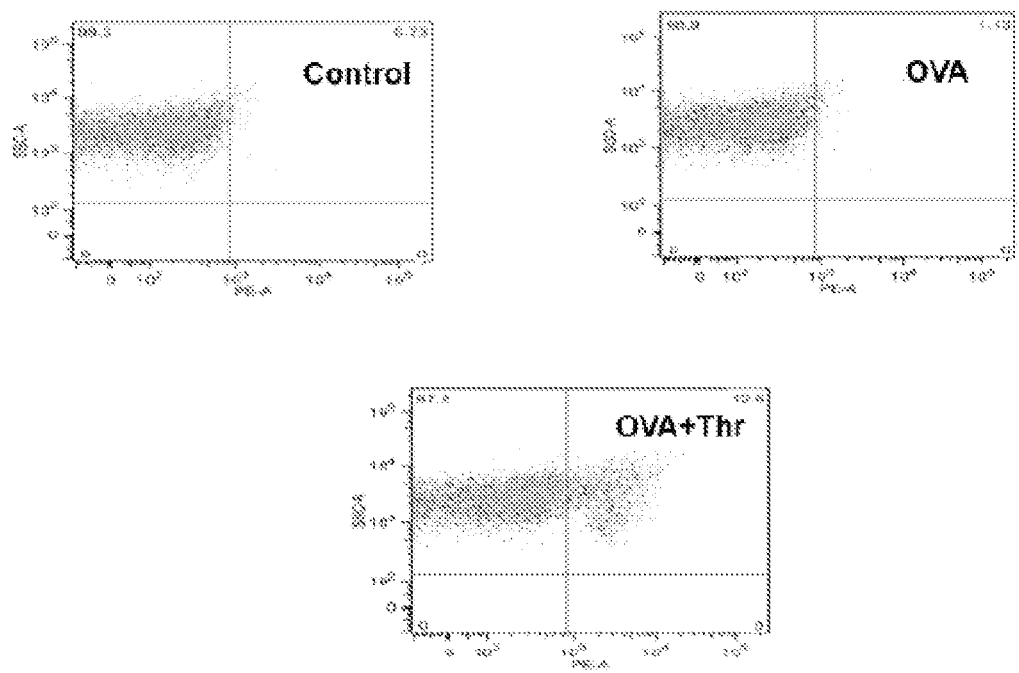
FIG. 2D shows FACS analysis of platelets incubated with OVA peptide alone or with OVA peptide and platelet stimulation.
Figure 2E:
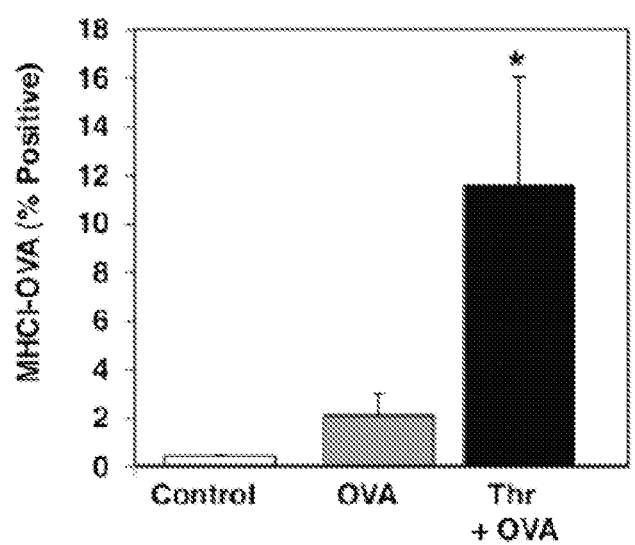
FIG. 2E is a graph demonstrating quantification of the FACS data of FIG. 2E (n=4±SD, *P<0.001 vs. OVA).
Figure 2F:
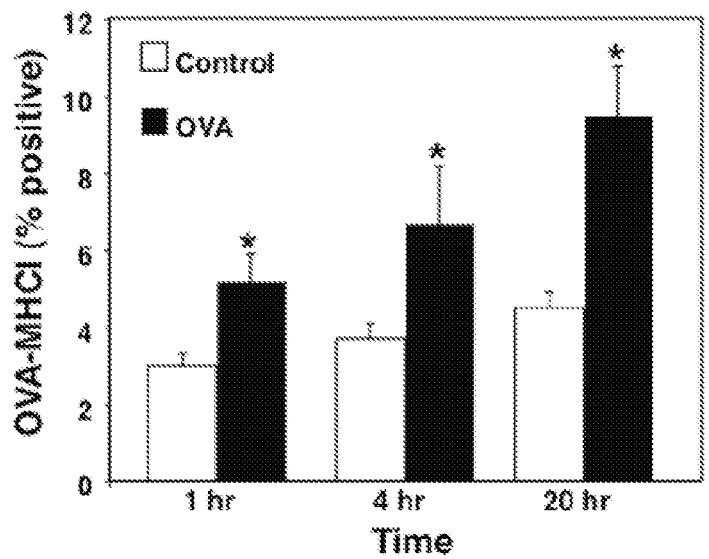
FIG. 2F is a graph demonstrating quantification of OVA-MHCI positive cells over time. Platelets were incubated with 200 µg/ml of OVA peptide alone or with platelet stimulation (0.1 U/ml thrombin) and OVA-MHCI was measured at multiple time points (n=4±SD, *P<0.004 vs. Control).
Figure 2G:
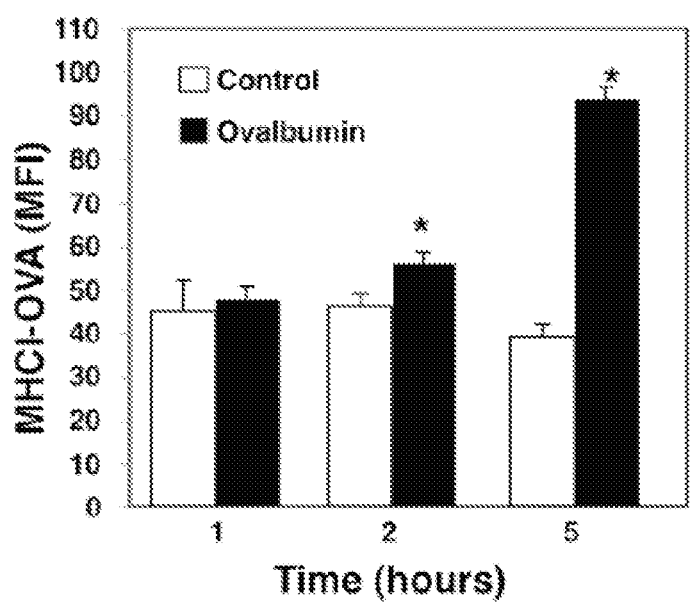
FIG. 2G is a graph demonstrating quantification of MHCI-OVA over time. Platelets were incubated with Ovalbumin, stimulated or not, and SIINFKL (SEQ ID NO:1) presentation was determined at multiple time points (n=4±SD, *P<0.007 and P=1.4×10$^{-6}$ vs. Control).
Figure 2H:
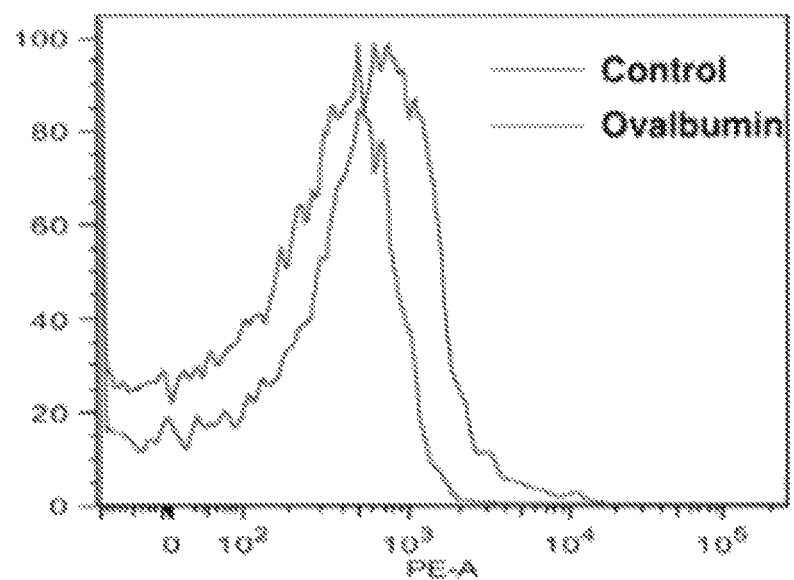
FIG. 2H shows a graph demonstrating that platelets present antigen. Platelets were incubated with full ovalbumin, stimulated or not and SIINFKL (SEQ ID NO:1) presentation was determined.

Platelets can be incubated with pathogens including viruses, such as HIV and dengue, and bacteria. To demonstrate platelet antigen processing capabilities, mouse platelets were washed and incubated with DQ-Ovalbumin, a protein with no fluorescence until it is cleaved, and platelet fluorescence was measured by flow cytometry. Platelets incubated with DQ-Ovalbumin had increased fluorescence indicating platelets may process antigen (FIG. 2C). To determine whether platelets present antigen, platelets from C57B16/J mice were incubated with the processed and $H2K^b$ MHC class I presented ovalbumin octapeptide SIINFEKL (SEQ ID NO:1). Platelets were then either activated with thrombin (0.1 U/mL) or were not activated. MHCI-SIINFEKL (SEQ ID NO:1) complex was measured by flow cytometry. MHC-OVA complex was noted with platelet stimulation (FIGS. 2D and 2E) and is increased with time (FIG. 2F). In addition, platelets incubated with full ovalbumin protein and stimulated also process and present ova peptide (FIGS. 2G and 2H). These data show that platelets have the ability to take up antigenic proteins and present the antigen in MHCI.

Figure 3A:
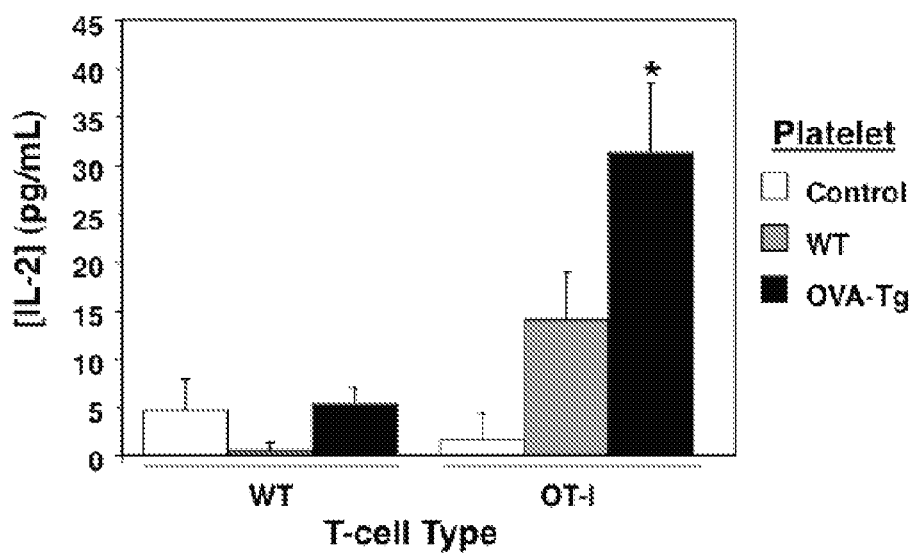
FIG. 3A is a graph demonstrating quantification of IL-2 expression levels. Wild type (WT) or OT-I T-cells were incubated with platelets from WT or OVA-Tg mice. IL-2 was measured by ELISA (n=4, *P=0.0005 vs. Control).
Figure 3B:
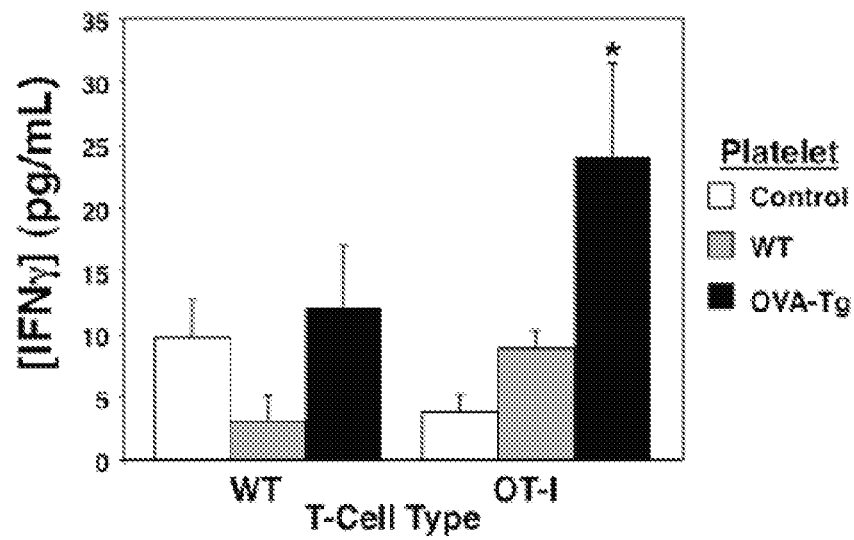
FIG. 3B is a graph demonstrating quantification of IFNγ expression levels. WT or OT-I T-cells were incubated with platelets from WT or OVA-Tg mice. IFNγ was measured by ELISA (n=4, *P=0.003 vs. Control).

Ovalbumin-transgenic (OVA-Tg) mice present self OVA antigen as part of normal immune tolerance development. Platelets from OVA-Tg mice activate T-cells from mice that are transgenic for T-cell receptors specific for OVA-MCH class I (OT-I mice, recognize ovalbumin residues 257-264 in the context of $H2K^b$). Wild type (WT) or OT-I T-cells were incubated with buffer, platelets from WT mice, or platelets from OVA-Tg mice and IL-2 production was measured overnight. INF-γ was measured 48 hours later by ELISA. OT-I T-cells incubated with platelets from OVA-Tg mice had greatly increased IL-2 and INF-γ compared to OT-I T-cells incubated with WT platelets (FIGS. 3A and 3B). These data indicate that platelets can present antigen and activate T-cells in vitro.

Figure 3C:
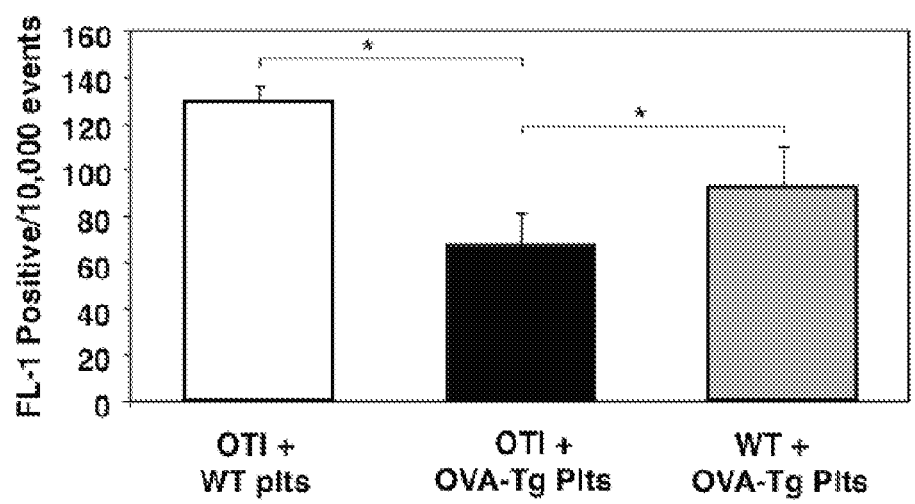
FIG. 3C is a graph demonstrating quantification of FL-1 Positive cells/10,000 events. WT or OT-I mice were given CFDA labeled WT or OVA-Tg platelets and 48 hours later blood was collected. The number of fluorescent platelets was determined by FACS (n=5, *P=0.01).
Figure 3D:
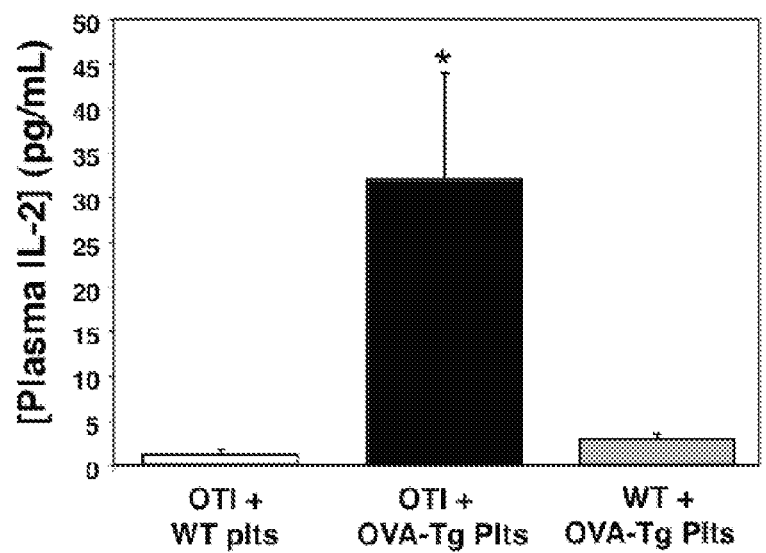
FIG. 3D is a graph demonstrating quantification of plasma IL-2 levels. WT or OT-I mice were given CFDA labeled WT or OVA-Tg platelets and 48 hours later blood was collected and plasma IL-2 levels were measured (n=4, *P=0.03).

To determine whether platelets present antigen and are targets of T-cells in vivo, OT-I mice were administered $1 \times 10^8$ CFDA labeled WT or OVA-Tg platelets intravenously (i.v.) (~1% total circulating platelets) and 48 hours later the number of circulating fluorescent platelets was determined by flow cytomentry. The number of OVA-Tg platelets in circulation was reduced by about 50% compared to WT platelets (FIG. 3C, white vs. black). As a control, OVA-Tg platelets were also labeled and injected into WT mice and these platelets had significantly less clearance compared to OVA-Tg platelets injected into OT-I mice (FIG. 3C, black vs gray). To demonstrate T-cell stimulation in vivo, plasma IL-2 was also measured, and it was found that only OVA-Tg platelets in OT-1 mice induced T-cell stimulation (FIG. 3D), demonstrating that platelets presenting antigen in MHC are targets of T-cells and stimulate T-cells in an antigen specific manner in vivo.

Figure 4A:
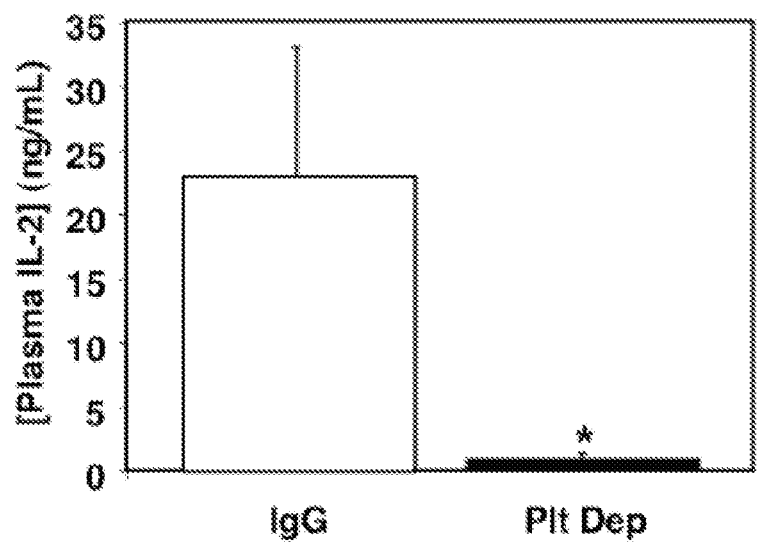
FIG. 4A is a graph demonstrating quantification of plasma IL-2 levels. Platelet depleted *P. berghei* infected mice have lower plasma IL-2 compared to control infected mice on day 4 (n=5, *P=0.009 vs. Control).
Figure 4B:
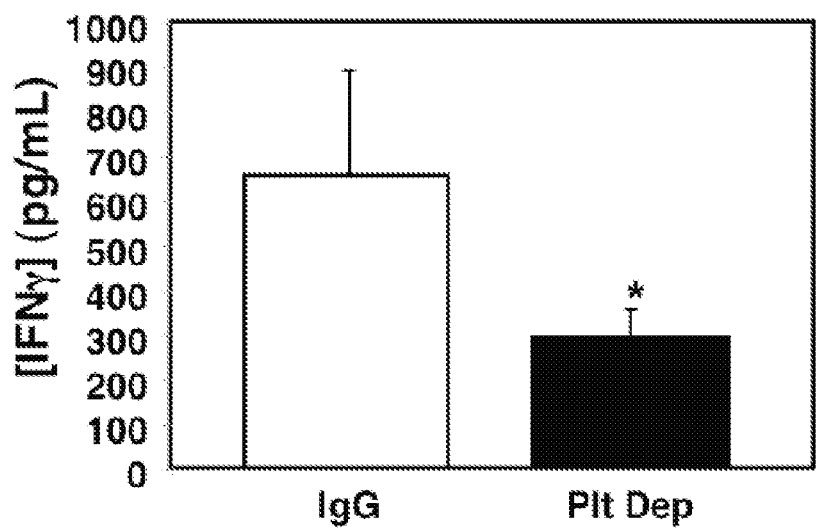
FIG. 4B is a graph demonstrating quantification of IFNγ levels in the same platelet depleted *P. bergheri* infected mice of FIG. 4A (n=4, *P<0.05 vs. Control).

Cerebral malaria (CM) is a severe complication of *Plasmodium falciparum* infection, particularly in children, and CM is the cause of significant morbidity and mortality in many parts of the world. CM is the result of a combination of vascular and immune system dysfunction and has been shown to be in part a $CD8^+$ T-cell dependent process (Hunt et al., Int. J. Parasitol. 36:569 (2006); Renia et al., Int. J. Parasitol. 36:547 (2006); Srivastava et al., PLoS One 5:e10413 (2010); Hafalla et al., Parasite Immunol. 28:15 (2006)). It has also been shown in the *P. berghei* ANKA experimental cerebral malaria (ECM) model that platelets have a role in initiating and sustaining the pathogenesis of ECM (van der Hyde et al., Blood 105:1956 (2005); van der Hyde et al., Trends Parasitol. 22:503 (2006)). Platelets also have a role in driving the T-cell response in ECM. Mice treated with platelet-depleting antibody 24 hours after *P. berghei* ANKA infection had greatly reduced plasma IL-2 and IFNγ in day 4 post infection compared to infected mice treated with control IgG (FIGS. 4A and 4B) demonstrating a role of platelets during in vivo T-cell responses to *P. berghei*.

Figure 4C:
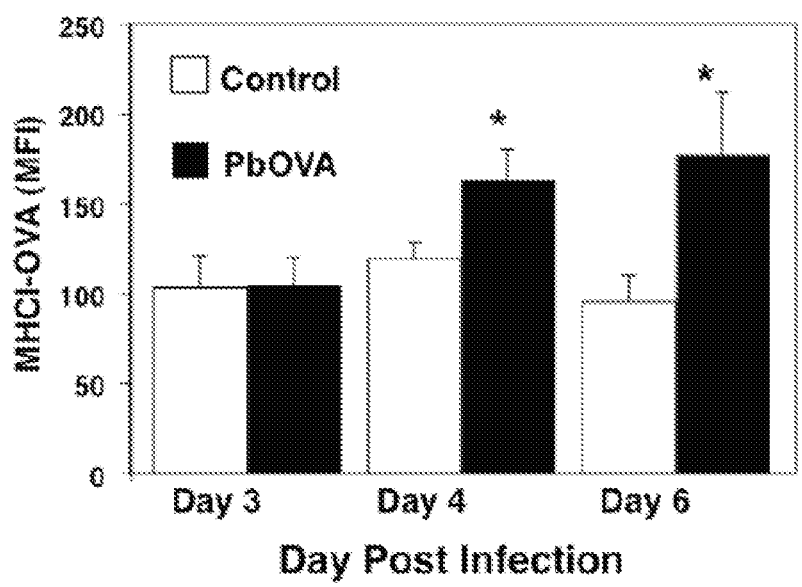
FIG. 4C is a graph demonstrating quantification of MHCI-OVA cells over time. Platelets present antigen in vivo. Platelets were isolated from control mice or mice infected with Pb-OVA, and MHCI-OVA was measured by FACS (n=5, *P=0.002 vs. Control).
Figure 4D:
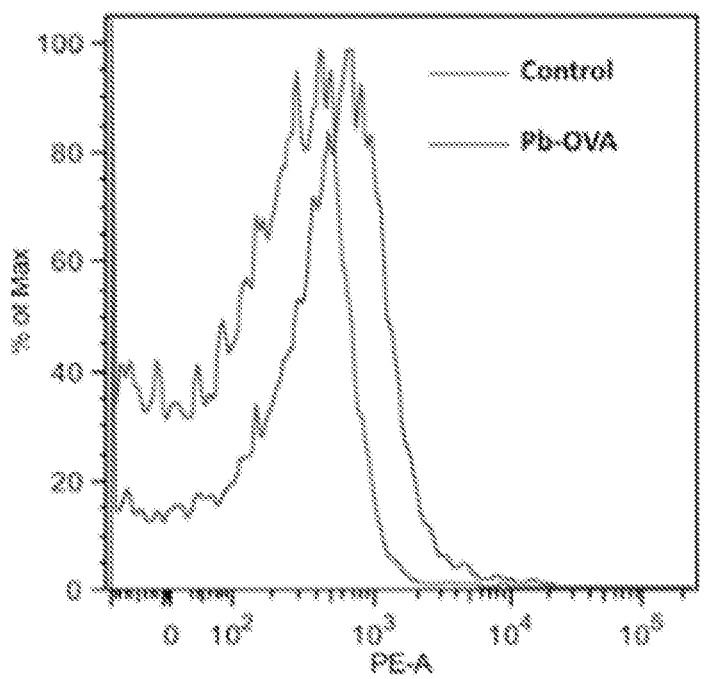
FIG. 4D shows a FACS analysis demonstrating that platelets present antigen in vivo. Platelets were isolated from control mice or mice infected with Pb-Ova, and MHCI-OVA was measured by FACS.

Platelets present malaria associated antigens. Mice were infected with *P. berghei* parasite that is transgenic for a truncated C-terminal fragment of ovalbumin (aa 150-386) (SEQ ID NO:2) fused to the N-terminal sequence (aa 1-5) MSVLG (SEQ ID NO:3) of the PbA heat shock protein (hsp) 70 gene (PbA-OVA) (Miyakoda et al., J. Immunol. 181:1420 (2008)). Platelets were isolated from control and infected mice to determine platelet MHCI-OVA complex expression using flow cytometry on days 3, 4 and 6 post infection. Beginning on day 4, platelets were noted to be MHC-OVA positive (FIG. 4C) demonstrating that platelets present parasite derived antigen.

Figure 4E:
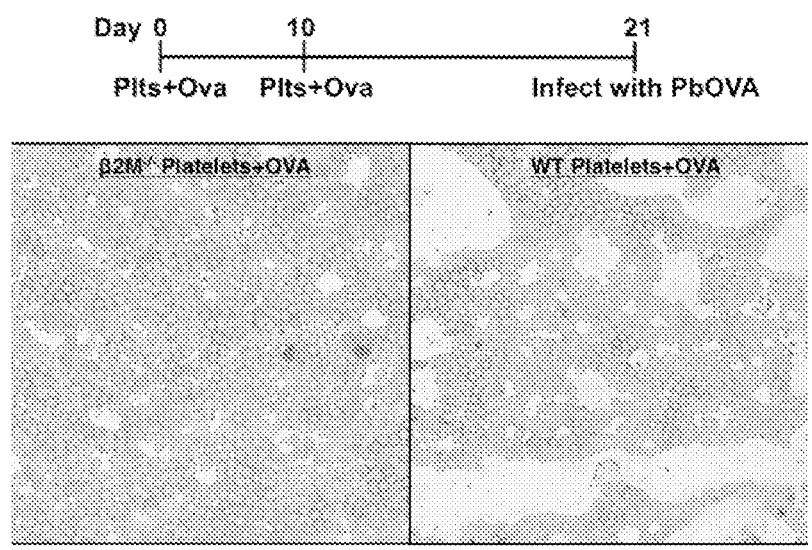
FIG. 4E shows microscopic images of platelets demonstrating that platelets can be used for cell based vaccines. Platelets from WT or $\beta 2M^{-/-}$ mice were incubated with SIINFEKL (SEQ ID NO:1), stimulated, and washed. $1\times10^7$ platelets were injected intravenously into WT mice. This was repeated 10 days later and mice were infected with Pb-OVA 21 days after the first injection. The representative images were taken 7 days post infection parasitemia.
Figure 4F:
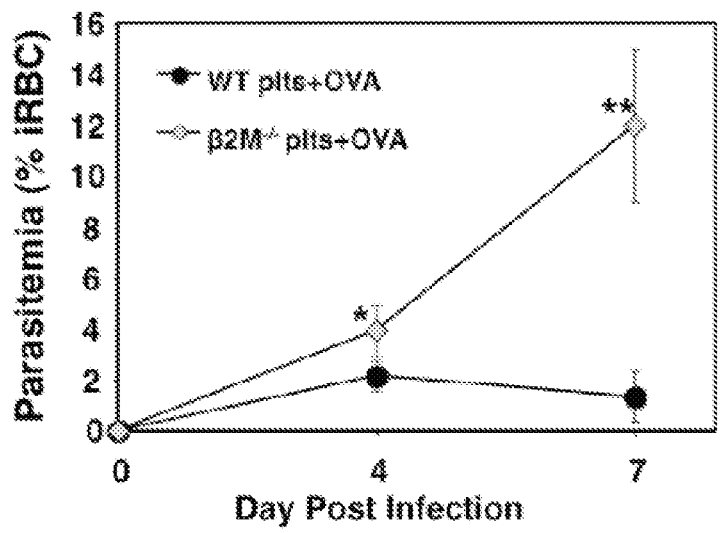
FIG. 4F is a graph demonstrating quantification of parasitemia (n=5, *P=0.004 day 4, 4.4×10-7 day 7 vs. WT).
Figure 4G:
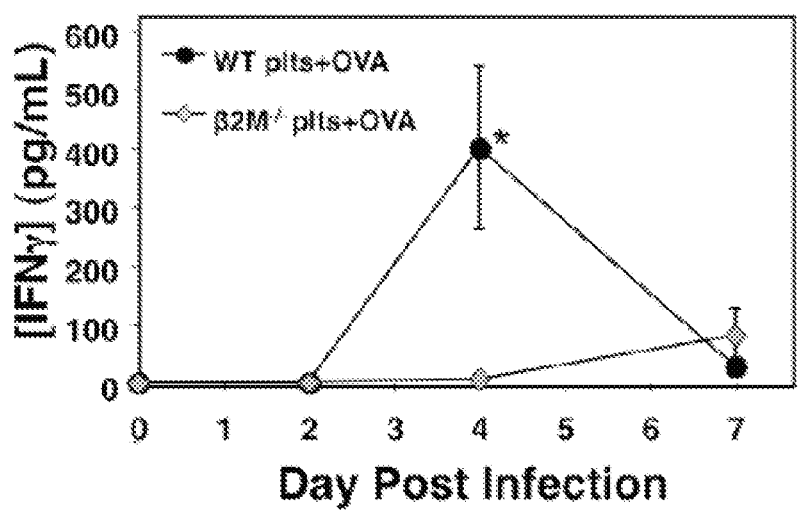
FIG. 4G is a graph demonstrating quantification of IFNγ over time (n=5, *P=0.00048 vs. WT).
Figure 4H:
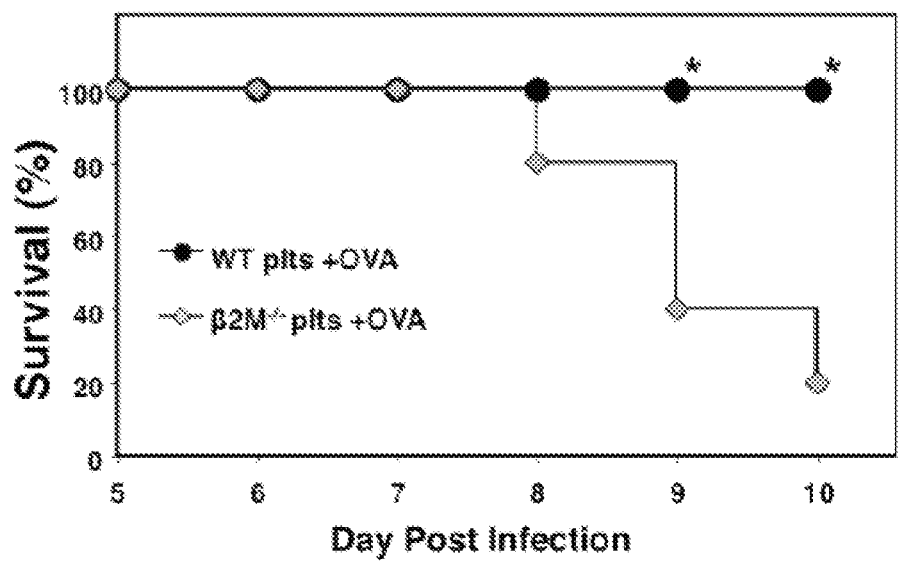
FIG. 4H is a graph demonstrating survival over time (n=5, *P=0.03 vs. WT).
Figure 4I:
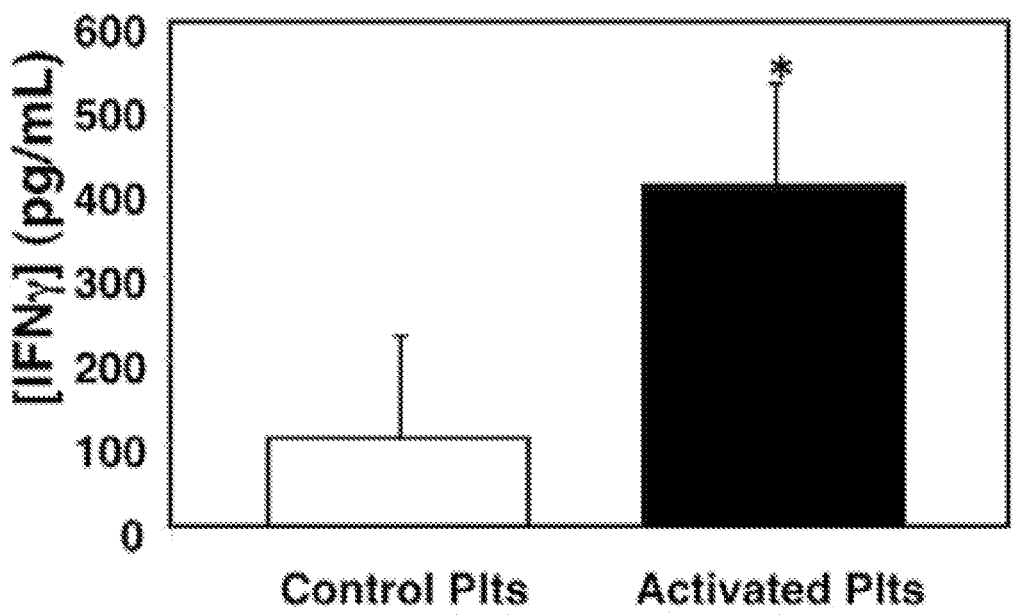
FIG. 4I is a graph demonstrating that platelets stimulate T-cells in vivo. IFNγ was measured (n=5, *P<0.01 vs control platelets).
Figure 4J:
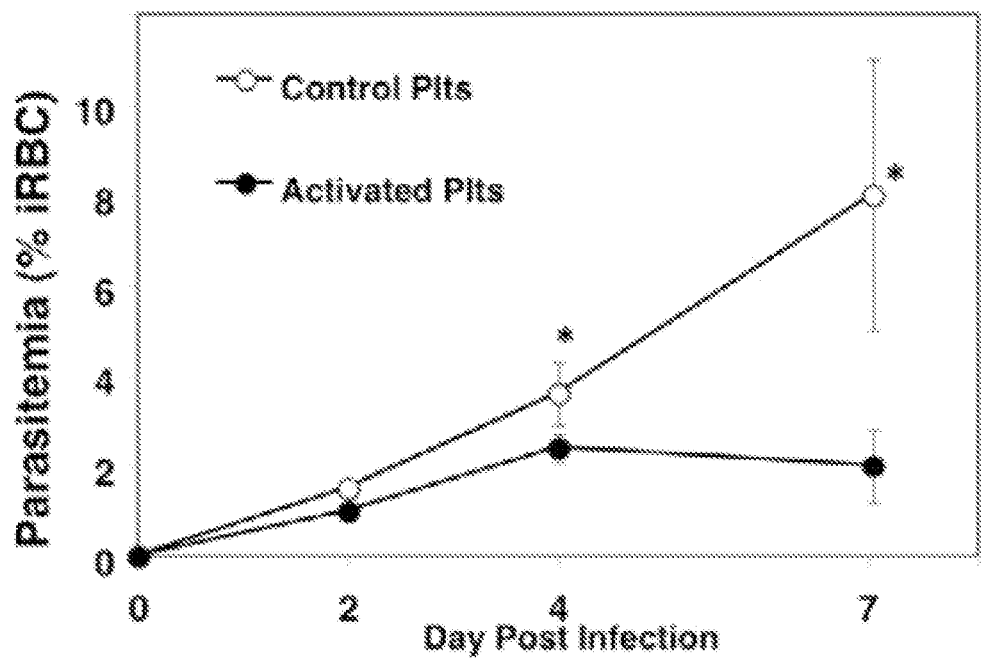
FIG. 4J is a graph demonstrating that platelets stimulate T-cells in vivo. Parasitemia was measured over 7 days (n=5, *P<0.05).
Figure 4K:
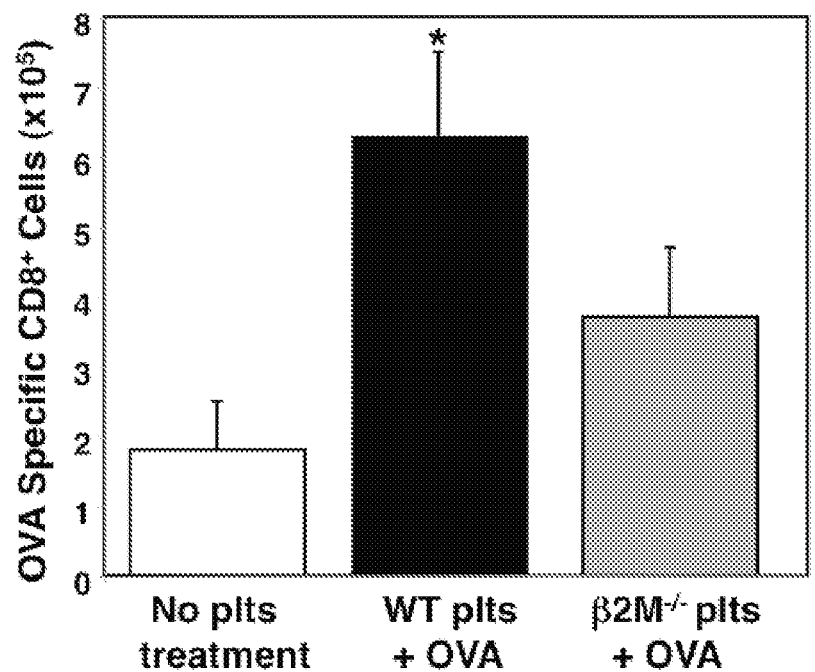
FIG. 4K is a graph showing the quantification of flow cytometry analysis of OVA specific CD8+ cells. Mononuclear cells were isolated from the spleens of mice on day 4 post-infection and the number of OVA specific T cells were quantified by flow cytometry (n=5±S.D., *P<0.03; vs. $\beta 2M^{-/-}$)

Platelet antigen presentation may provide a means to develop vaccine strategies. To test this concept, WT platelets or platelets from MHC class I deficient mice (P2 microglobulin knockout, ($β2M^{-/-}$) were treated with OVA peptide (300 µg/mL), activated with mild thrombin stimulation, and incubated for 2 hours. $1 \times 10^7$ platelets were then injected intravenously (i.v.) into WT mice. This was repeated 10 days later, and 21 days after the first injection mice were infected with PbA-OVA. Mice that received the WT platelet/OVA vaccine had a significantly reduced parasite burden (% infected RBC, iRBC) compared to control mice that received the $β2M^{-/-}$ platelet vaccine, particularly after day 4 post infection (FIGS. 4E and 4F). On day 4 post infection, the WT platelet/OVA mice also had greatly increased plasma IFNγ that declined by day 7 mirroring the time point at which the parasitemia diverged between the two groups (FIG. 4G). WT platelet/OVA mice also had a greatly improved survival compared to ($32M^{-/-}$ controls (FIG. 4F). The WT platelet/OVA vaccine mice eventually become anemic and die about day 20, but their parasitemia does not reach high levels. Mice were also sacrificed on day 4 post-infection and OVA specific $CD8^+$ cells in the spleen were quantified by FACS using a MHC class I pentamer. PbA-OVA infected mice that received no platelet treatment developed a low number of OVA specific T cells (FIG. 4K, white bar). Mice treated with the WT platelet/OVA regimen had a greatly increased number of OVA specific T cells compared to mice treated with the $β2M^{-/-}$ platelet OVA (FIG. 4K), demonstrating that platelets induce a specific T cell response in a manner dependent on platelet MHCI. As an additional control, the studies were repeated using WT platelets incubated with OVA and the platelets were activated or were left resting before washing (resting platelets do not appear to present antigen). Results of this study were very similar. These data demonstrate that platelets present antigen to T-cells in a MHC class I dependent manner to induce a naïve T-cell response.

Figure 5A:
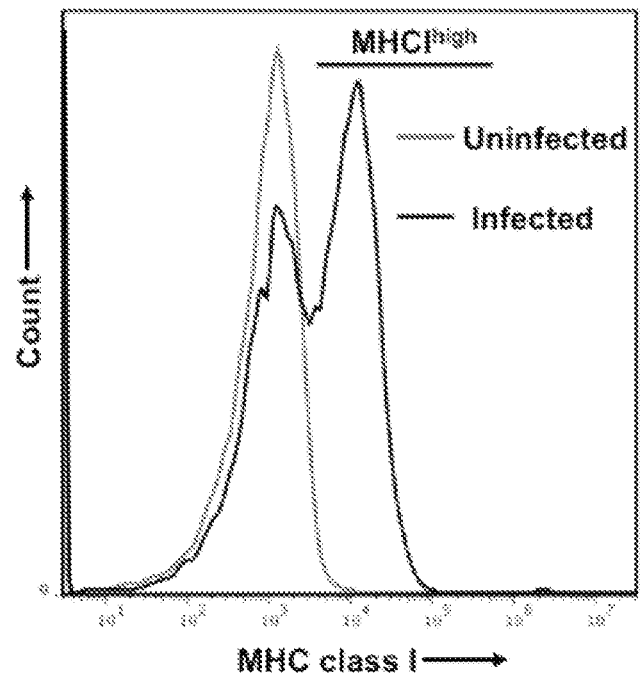
FIG. 5A is a FACS analysis demonstrating that MHCI expression is increased in platelets from *P. berghei* infected mice. Platelets were isolated from infected mice on day 6 post infection and MHCI expression determined by FACS.
Figure 5B:
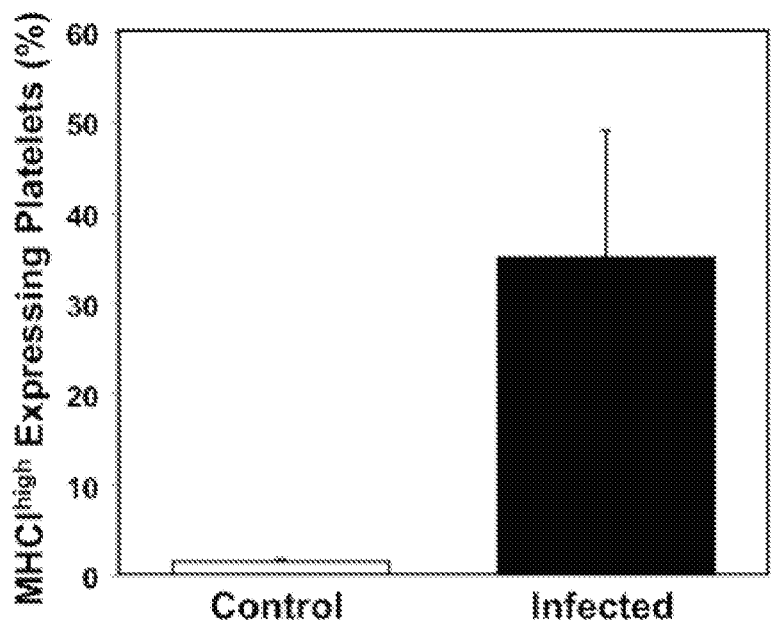
FIG. 5B is a graph of the quantification of $MHCI^{high}$ expressing platelets (n=5±S.D., *P<0.01 vs Uninfected).

MHCI expression is often increased on non-professional antigen presenting cells during infectious processes. Platelets from uninfected control mice and *P. berghei* infected mice were isolated on days 4 and 6 post-infection to determine whether platelet MHCI expression is increased in ECM. On day 4 post infection MHCI expression was only slightly increased; however, by day 6 there was a population of platelets that expressed greatly increased levels of MHCI (these platelets are denoted $MHCI^{hi}$ platelets) (FIGS. 5A and 5B). These data demonstrate that platelets increase MHCI expression during infection.

Figure 5C:
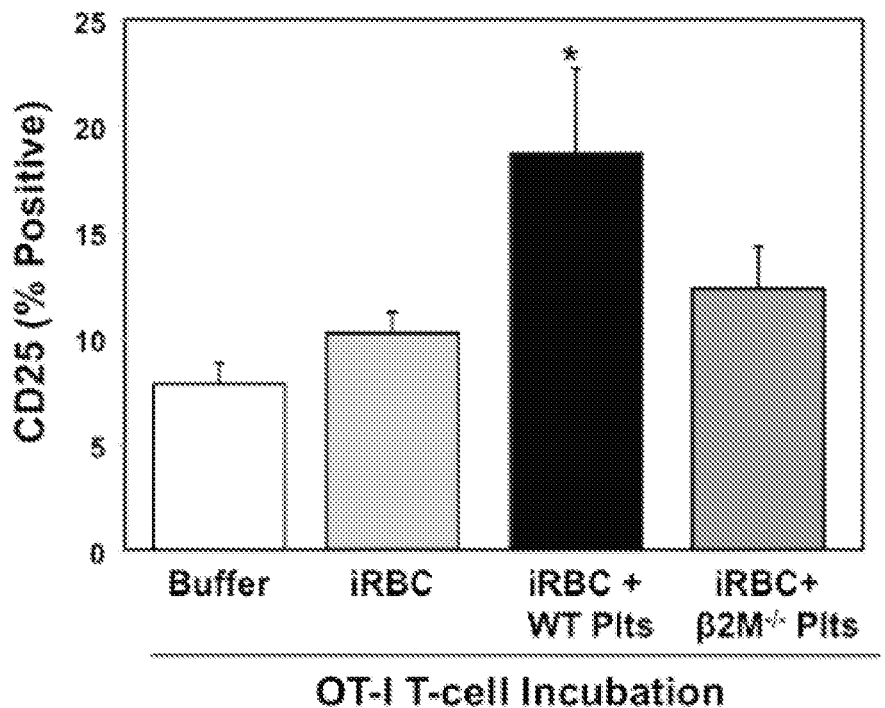
FIGS. 5C and 5D are graphs demonstrating that platelets acquire and present antigen. OT-I T cells were incubated alone, with iRBC (infected RBC), or with iRBC and WT or $\beta 2M^{-/-}$ platelets. 48 hours later T cell CD25 (IL-2R) and IL-2 expression was determined by FACS. An increase in CD25 expression (n=4±S.D., *P<0.02 vs iRBC) and G) (FIG. 5C) and IL-2 production (n=4±S.D., *P<0.03 vs iRBC) (FIG. 5D) was observed.
Figure 5D:
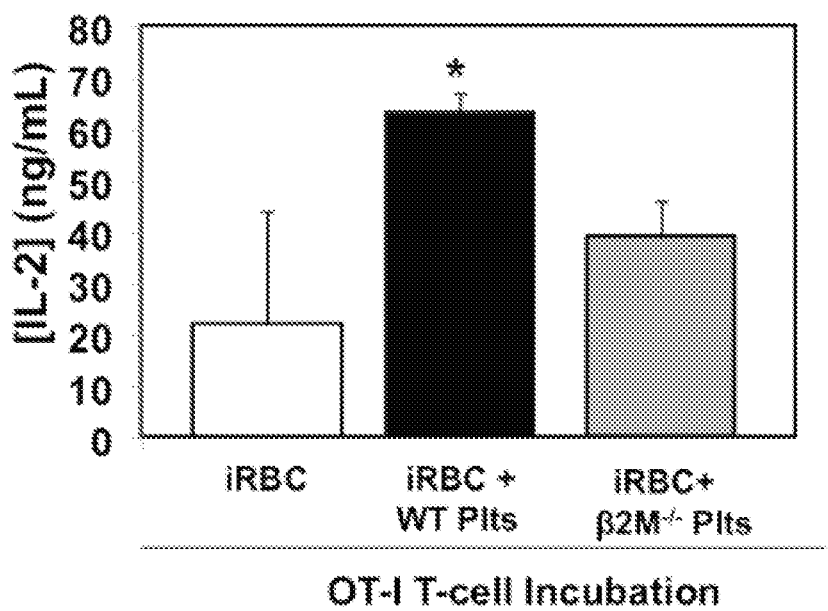

To more directly demonstrate that platelets present *Plasmodium* antigen to T cells, MHC class I deficient $β2M^{-/-}$ mice were infected with PbA-OVA and RBCs were isolated from infected mice on day 5 post infection. RBCs were then incubated with OT-I T cells only, OT-I T cells and WT platelets, or OT-I T cells and $β2M^{-/-}$ platelets (note: RBCs came from infected $β2M^{-/-}$ mice to eliminate the potential for contaminating antigen presenting platelets or leukocytes with the iRBC). T cell stimulation was determined 48 hours later by measuring CD25 expression using flow cytometry and IL-2 production by ELISA. Compared to the T cell and iRBC co-incubation, T cells incubated with iRBC and WT platelets, but not $β2M^{-/-}$ platelets, had significantly increased T cell activation (FIGS. 5C and 5D). These data demonstrate that platelets acquire and present parasite antigen to T cells in a platelet MHCI dependent manner.

Figure 6A:
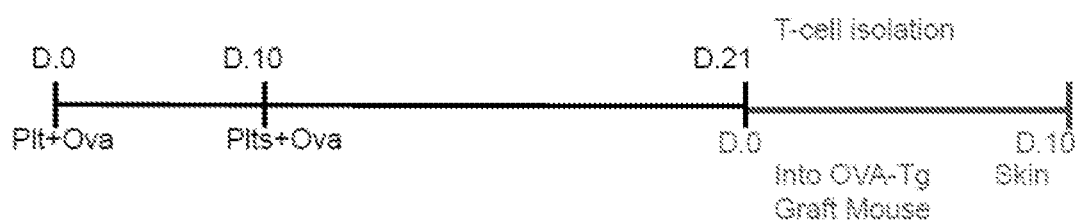
FIG. 6A is a diagram of the timeline for the experimental method.

To demonstrate that platelets can be used as a platform to stimulate naïve T cells in vivo in a different model system, platelets were isolated from WT and MHC$^{-/-}$ ($\beta$2M$^{-/-}$) mice. The platelets were incubated with 300 μg of OVA peptide and stimulated with 0.2 units (U)/ml of thrombin. Platelets and OVA were then incubated at room temperature for 2 hours, washed and 1×10$^7$ platelets were injected intravenously into recipient WT mice. 10 days later this was repeated, and 21 days after the first infection, T cells were isolated from the WT platelet/OVA (plt/OVA) and $\beta$2M$^{-/-}$ plt/OVA treated mice (FIG. 6A). A separate set of nude mice were given skin grafts with skin from OVA-transgenic mice and bandaged for 7 days to allow for vascular connections. Mice were then unbandaged and reconstituted intravenously with 1×10$^6$ T cells from either the WT plt/OVA mice or $\beta$2M$^{-/-}$ plt/OVA mice. Blood was collected from the T cell reconstituted mice, plasma was isolated, and IFN$\gamma$ was measured by ELISA.

Figure 6B:
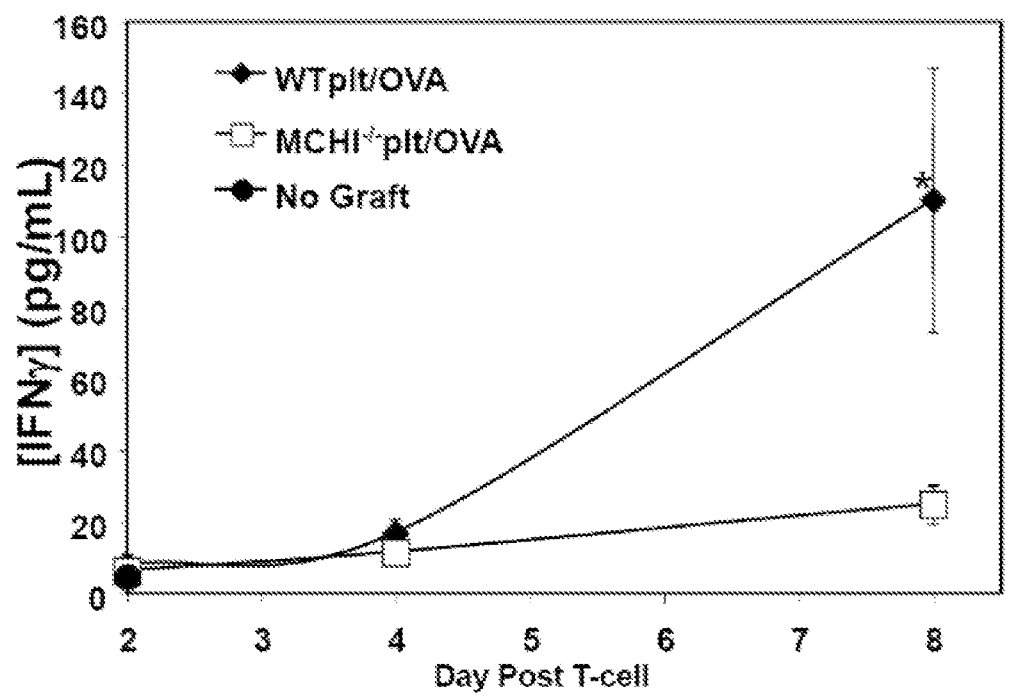
FIG. 6B is a graph demonstrating that T cells from WT platelet vaccination mice have a more vigorous transplant immune response to OVA-Tg skin graft, as IFNγ levels are increased in the skin graft mice receiving T cells from the WT platelet-OVA treated mice.
Figure 6C:
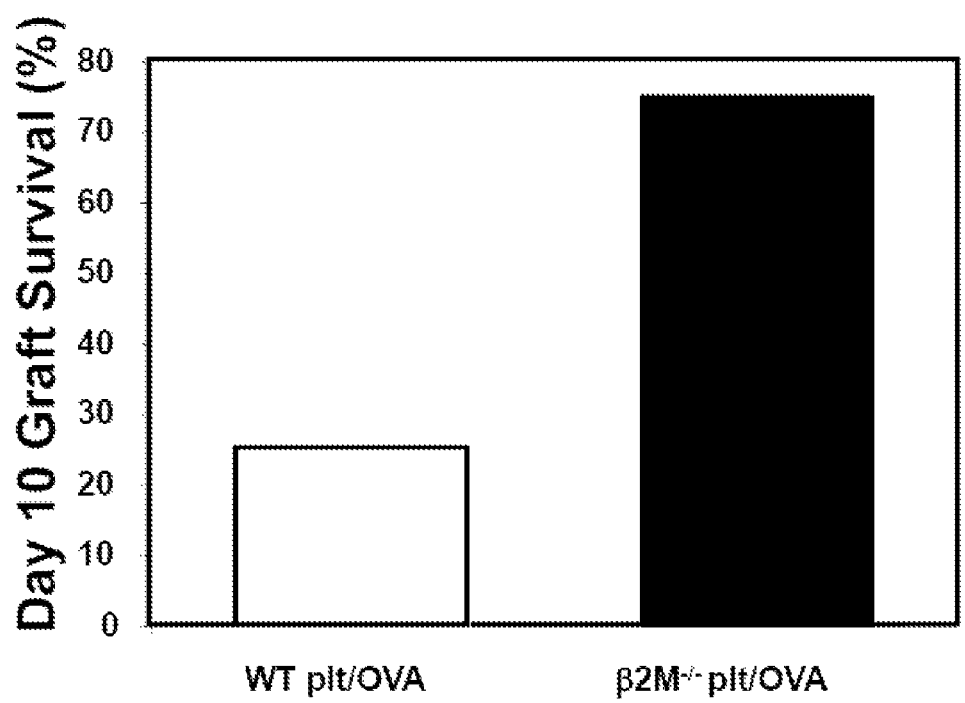
FIG. 6C is a graph demonstrating that skin graft mice that receive T cells from the WT-platelet-OVA treated mice rejected OVA-Tg skin grafts more rapidly.

Graft rejection was also monitored by assessment of graft health using visual parameters such as scabbing and darkening of the skin graft. Mice with OVA-Tg skin grafts that received T cells from WT plt/OVA treated mice had increased IFN$\gamma$ (FIG. 6B) and decreased graft survival (FIG. 6C) compared to mice that received T cells from mice treated with $\beta$2M$^{-/-}$ plt/OVA platelets. These data support the results that platelets can be used to stimulate naïve T cells in an MHC dependent manner.

In summary, platelets express the molecules necessary to be an APC and present antigen to T-cells. Platelet APC function is important in the pathogenesis of cerebral malaria and can be used in the design of novel therapeutic strategies, such as platelet based vaccines using platelets. This novel role for platelets may be extended to many blood bourne infections and vascular inflammatory diseases as well as the design of cell based vaccine strategies.

What is claimed is:

1. A method of eliciting an immune response in a subject, the method comprising:
   a. providing antigen-presenting platelets, wherein the platelets present a selected antigen; and
   b. administering to the subject the antigen-presenting platelets, wherein administration of the antigen-presenting platelets elicits an immune response in the subject, wherein the antigen-presenting platelets are of the same species as the subject.

2. The method of claim 1, wherein the antigen-presenting platelets are administered to the subject at least two times.

3. The method of claim 2, wherein the second administration of antigen-presenting platelets is at least five, six, seven, eight, nine, ten, eleven, twelve, thirteen, or fourteen days after the first administration.

4. The method of claim 1, further comprising administering an adjuvant to the subject.

5. The method of claim 1, wherein the antigen-presenting platelets are produced by platelets isolated from the same subject.

6. The method of claim 1, wherein the antigen-presenting platelets are produced by platelets isolated from a different subject.

7. The method of claim 1, wherein the method further comprises administering to the subject an antigen-presenting cell.

8. The method of claim 7, wherein the antigen-presenting cell is a dendritic cell.

* * * * *